(12) United States Patent
Sode

(10) Patent No.: US 7,960,156 B2
(45) Date of Patent: Jun. 14, 2011

(54) GLUCOSE DEHYDROGENASE AND METHOD FOR PRODUCING THE DEHYDROGENASE

(76) Inventor: Koji Sode, Tokyo (JP)

( * ) Notice: Subject to any disclaimer, the term of this patent is extended or adjusted under 35 U.S.C. 154(b) by 0 days.

(21) Appl. No.: 12/764,794

(22) Filed: Apr. 21, 2010

(65) Prior Publication Data

US 2010/0285566 A1     Nov. 11, 2010

Related U.S. Application Data

(62) Division of application No. 11/835,216, filed on Aug. 7, 2007, now Pat. No. 7,867,742, which is a division of application No. 10/415,504, filed as application No. PCT/JP01/09556 on Oct. 31, 2001, now Pat. No. 7,741,090.

(30) Foreign Application Priority Data

| Oct. 31, 2000 | (JP) | ................................ | 2000-332085 |
| Nov. 24, 2000 | (JP) | ................................ | 2000-357102 |
| Sep. 12, 2001 | (JP) | ................................ | 2001-276832 |

(51) Int. Cl.
| C12N 9/02 | (2006.01) |
| C12N 1/20 | (2006.01) |
| C12N 15/00 | (2006.01) |
| C07P 21/02 | (2006.01) |
| C12P 21/06 | (2006.01) |

(52) U.S. Cl. .................. 435/189; 435/252.3; 435/320.1; 435/69.1; 536/23.1

(58) Field of Classification Search .......................... None
See application file for complete search history.

(56) References Cited

FOREIGN PATENT DOCUMENTS

| EP | 0 477 788 | 4/1992 |
| JP | 11-243949 | 9/1999 |
| WO | WO 03/091430 | 11/2003 |

OTHER PUBLICATIONS

ATCC Catalogue, ATCC Bacteria and Bacteriophages. 19$^{th}$ edition. 1996, pp. 78, 79 and 286.
Estanol, et al. "Inorganic Phosphate Effect on Alternate Peripheral Pathways of Glucose Catabolism in *Pseudomonas cepacia*," *Federation of European Microbiological Societies Letters*, vol. 60, pp. 295-298, 1989.
Sage, et al. "Hexose Phosphate Metabolism and Exopolysaccharide Formation in *Pseudomonas cepacia*," *Current Microbiology*, vol. 20, pp. 191-198, 1990.
Inose, et al. "Cloning and Expression of the Gene Encoding Catalytic Subunit of Thermostable Glucose Dehydrogenase fro *Burkholderia cepacia* in *Escherichia coli*," *Biochemica et Biophysica Acta*, vol. 1645, pp. 133-138, 2003.
Sode, et al. "A Novel Thermostable Glucose Dehydrogenase Varying Temperature Properties by Altering Its Quatemary Structures," *Enzyme and Microbial Technology*, vol. 19, pp. 82-85, 1996.
Yamazaki, et al. "Increased Thermal Stability of Glucose Dehydrogenase by Cross-Linking Chemical Modification," *Biotechnology Letters*, vol. 21, pp. 199-202, 1999.
Yamazaki, et al. "Subunit Analysis of a Novel Thermostable Glucose Dehydrogenase Showing Different Temperature Properties According to its Quatemary Structure," *Applied Biochemistry and Biotechnology*, vol. 77-79, pp. 325-335, 1999.
Yum, et al. "Cloning and Expression of a Gene Cluster Encoding Three Subunits of Membrane-Bound Gluconate Dehydrogenase from *Erwinia cypripedii* ATCC 29267 in *Escherichia coli*," *Journal of Bacteriology*, pp. 6566-6572, Nov. 1997.
Yabuuchi, Eiko, et al. "Proposal of *Burkholderia* gen. nov. and Transfer of Seven Species of the Genus *Pseudomonas* Homology Group II to the New Genus, with the Type Species *Burkholderia cepacia* (Palleroni and Holmes 1981) comb. nov.," *Microbiol. Immunol.*, 36(12) 1251-1275, 1992.

*Primary Examiner* — Tekchand Saidha
*Assistant Examiner* — Younus Meah
(74) *Attorney, Agent, or Firm* — Knobbe, Martens, Olson & Bear, LLP

(57) ABSTRACT

A DNA encoding a glucose dehydrogenase enzyme with high substrate specificity and recombinant vectors and transformants for expression of the DNA are disclosed. By culturing the transformant, the glucose dehydrogenase enzyme can be produced at a low cost. The glucose dehydrogenase enzyme produced is not affected by oxygen dissolved in a measurement sample and, in particular, has superior thermal stability.

8 Claims, 6 Drawing Sheets

US 7,960,156 B2

GLUCOSE DEHYDROGENASE AND METHOD FOR PRODUCING THE DEHYDROGENASE

RELATED APPLICATIONS

This application is a divisional of U.S. application Ser. No. 11/835,216, filed Aug. 7, 2007, now U.S. Pat. No. 7,867,742, which is a divisional of U.S. application Ser. No. 10/415,504, filed Jul. 3, 2003, now U.S. Pat. No. 7,741,090 both of which are incorporated herein by reference. U.S. application Ser. No. 10/415,504, filed Jul. 3, 2003 is the U.S. National Phase under 35 U.S.C. §371 of International Application PCT/JP01/09556, filed Oct. 31, 2001, which was published in the Japanese language which claims the priority of Japanese Application No. 2001-276832, filed Sep. 12, 2001; Japanese Application No. 2000-357102, filed Nov. 24, 2000; and Japanese Application No. 2000-332085, filed Oct. 31, 2000.

TECHNICAL FIELD

The present invention relates to a novel glucose dehydrogenase and a method for producing the same, a DNA encoding the enzyme, a recombinant vector comprising the DNA encoding the enzyme, a transformant transformed with the recombinant vector, a novel microorganism producing the enzyme, a glucose sensor using an enzyme electrode including the enzyme, the transformant or the microorganism, and a glucose assay kit.

BACKGROUND ART

Biosensors using an enzyme that specifically reacts with a particular substrate are being actively developed in various industrial fields. As for a glucose sensor, which is one of the biosensors, in particular, measurement methods and devices utilizing such methods are being actively developed mainly in medical fields.

The glucose sensor has a history of about 40 years since Clark and Lyons first reported about a biosensor comprising glucose oxidase and an oxygen electrode in combination in 1962 (L.c. Clark, J. and Lyonas, C. "Electrode systems for continuous monitoring in cardiovascular surgery." Ann. n.y. Acad. Sci., 105: 20-45).

Thus, the adoption of glucose oxidase as an enzyme of the glucose sensor has a long history. This is because glucose oxidase shows high substrate specificity for glucose and superior thermal stability, this enzyme can further be produced in a large scale, and its production cost is lower than those of other enzymes.

The high substrate specificity means that this enzyme does not react with a saccharide other than glucose, and this leads to an advantage that accurate measurement can be achieved without error in measurement values.

Further, the superior thermal stability means that problems concerning denaturation of the enzyme and inactivation of its enzymatic activity due to heat can be prevented, and this leads to an advantage that accurate measurement can be performed over a long period of time.

However, although glucose oxidase has high substrate specificity and superior thermal stability and can be produced at a low cost, it has a problem that the enzyme is affected by dissolved oxygen as described below and this affects measurement results.

Meanwhile, in addition to glucose oxidase, a glucose sensor utilizing glucose dehydrogenase has also been developed. This enzyme is also found in microorganisms.

For example, there are known glucose dehydrogenase derived from *Bacillus* bacteria (EC 1.1.1.47) and glucose dehydrogenase derived from *Cryptococcus* bacteria (EC 1.1.1.119).

The former glucose dehydrogenase (EC 1.1.1.47) is an enzyme that catalyzes a reaction of β-D-glucose+NAD(P)$^+$→D-δ-gluconolactone+NAD(P)H+H$^+$, and the latter glucose dehydrogenase (EC1.1.1.119) is an enzyme that catalyzes a reaction of D-glucose+NADP$^+$→D-δ-gluconolactone+NADPH+H. The aforementioned glucose dehydrogenases derived from microorganisms are already marketed.

These glucose dehydrogenases have an advantage that they are not affected by oxygen dissolved in a measurement sample. This leads to an advantage that accurate measurement can be achieved without causing errors in measurement results even when the measurement is performed in an environment in which the oxygen partial pressure is low, or a high-concentration sample requiring a large amount of oxygen is used for the measurement.

However, although glucose dehydrogenase is not affected by dissolved oxygen, it has problems of poor thermal stability and substrate specificity poorer than that of glucose oxidase.

Therefore, an enzyme that overcomes disadvantages of both of glucose oxidase and glucose dehydrogenase has been desired.

The inventors of the present invention reported results of their studies about glucose dehydrogenase using samples collected from soil near hot springs in Sode K., Tsugawa W., Yamazaki T., Watanabe M., Ogasawara N., and Tanaka M., Enzyme Microb. Technol., 19, 82-85 (1996); Yamazaki T., Tsugawa W. and Sode K., Appli. Biochemi. and Biotec., 77-79/0325 (1999); and Yamazaki T., Tsugawa W. and Sode K., Biotec. Lett., 21, 199-202 (1999).

However, a bacterial strain having oxygen-producing ability had not been identified at the stage of these studies.

DISCLOSURE OF THE INVENTION

An object of the present invention is to provide an enzyme that overcomes the disadvantages of both of known glucose oxidase and glucose dehydrogenase, i.e., an enzyme that shows high substrate specificity and superior thermal stability, can be produced at a low cost and is not affected by oxygen dissolved in a measurement sample.

Further, another object of the present invention is to provide a method for producing the aforementioned enzyme, a protein utilizing characteristics of the enzyme and a novel microorganism producing the enzyme.

A further object of the present invention is to provide a DNA encoding the aforementioned enzyme, a recombinant vector containing the DNA encoding the enzyme and a transformant transformed with the recombinant vector.

A still further object of the present invention is to provide a glucose sensor using an enzyme electrode including the aforementioned enzyme, transformant or microorganism and a glucose assay kit including the aforementioned enzyme.

The inventors of the present invention successfully isolated *Burkhorderia cepacia* producing an enzyme achieving the aforementioned objects from soil near hot springs, and thus accomplished the present invention.

Thus, the present invention provides the followings.

(1) A method for producing glucose dehydrogenase comprising the steps of culturing a microorganism belonging to the genus *Burkhorderia* and having glucose dehydrogenase producing ability in a medium, and collecting glucose dehydrogenase from the medium and/or cells of the microorganism.
(2) The method for producing glucose dehydrogenase according to (1), wherein the microorganism is *Burkhorderia cepacia*.
(3) The method for producing glucose dehydrogenase according to (1) or (2), wherein the glucose dehydrogenase has the following properties:
(i) the enzyme has an action of catalyzing dehydrogenation reaction of glucose;
(ii) the enzyme consists of subunits showing a molecular weight of about 60 kDa and a molecular weight of about 43 kDa in SDS-polyacrylamide gel electrophoresis under a reducing condition;
(iii) the enzyme shows a molecular weight of about 380 kDa in gel filtration chromatography using TSK Gel G3000SW (Tosoh Corporation); and
(iv) the enzyme shows an optimal reaction temperature around 45° C. (Tris-HCl buffer, pH 8.0).
(4) The method for producing glucose dehydrogenase according to (3), wherein the subunit showing a molecular weight of about 43 kDa is an electron-transferring protein.
(5) The method for producing glucose dehydrogenase according to (4), wherein the electron-transferring protein is cytochrome C.
(6) A glucose dehydrogenase, which can be produced by a microorganism belonging to the genus *Burkhorderia*.
(7) The glucose dehydrogenase according to (6), wherein the microorganism is *Burkhorderia cepacia*.
(8) The glucose dehydrogenase according to (6) or (7), wherein the glucose dehydrogenase has the following properties:
(i) the enzyme has an action of catalyzing dehydrogenation reaction of glucose;
(ii) the enzyme consists of subunits showing a molecular weight of about 60 kDa and a molecular weight of about 43 kDa in SDS-polyacrylamide gel electrophoresis under a reducing condition;
(iii) the enzyme shows a molecular weight of about 380 kDa in gel filtration chromatography using TSK Gel G3000SW (Tosoh Corporation); and
(iv) the enzyme shows an optimal reaction temperature around 45° C. (Tris-HCl buffer, pH 8.0).
(9) The glucose dehydrogenase according to (8), wherein the subunit showing a molecular weight of about 43 kDa is an electron-transferring protein.
(10) The glucose dehydrogenase according to (9), wherein the electron-transferring protein is cytochrome C.
(11) The glucose dehydrogenase according to any one of (8) to (10), wherein the subunit showing a molecular weight of about 60 kDa comprises the amino acid sequence of the amino acid numbers 2 to 12 in SEQ ID NO: 3.
(12) The glucose dehydrogenase according to any one of (8) to (11), wherein the N-terminus of the subunit showing a molecular weight of 43 kDa has the amino acid sequence of SEQ ID NO: 5.
(13) The glucose dehydrogenase according to (11), wherein the subunit showing a molecular weight of about 60 kDa is a protein defined in the following (A) or (B):
(A) a protein which has the amino acid sequence of SEQ ID NO: 3;
(B) a protein which has the amino acid sequence of SEQ ID NO: 3 including substitution, deletion, insertion or addition of one or several amino acid residues and a glucose dehydrogenase activity.
(14) The glucose dehydrogenase according to (6), which shows activity peaks around 45° C. and around 75° C.

(15) A cytochrome C, which is a subunit of the glucose dehydrogenase according to (10) and has the amino acid sequence of SEQ ID NO: 5.
(16) A DNA encoding a part of the cytochrome C according to (15) and having the nucleotide sequence of SEQ ID NO: 8.
(17) A DNA encoding a part of the cytochrome C according to (15) and having the nucleotide sequence of the nucleotide numbers 2386 to 2467 in the nucleotide sequence of SEQ ID NO: 1.
(18) A DNA encoding a signal peptide of the cytochrome C according to (15) and comprising the nucleotide sequence of the nucleotide numbers 2386 to 2451 in the nucleotide sequence of SEQ ID NO: 1.
(19) A peptide which is a signal peptide of cytochrome C and has the amino acid sequence of the amino acid numbers 1 to 22 in the amino acid sequence of SEQ ID NO: 4.
(20) A protein having the following properties:
(i) the protein can constitute the glucose dehydrogenase according to (6) as a subunit;
(ii) the protein has a glucose dehydrogenase activity;
(iii) the protein shows a molecular weight of about 60 kDa in SDS-polyacrylamide gel electrophoresis under a reducing condition; and
(iv) the protein shows an optimal reaction temperature around 75° C. (Tris-HCl buffer, pH 8.0).
(21) The protein according to (20), which comprises the amino acid sequence of the amino acid numbers 2 to 12 in SEQ ID NO: 3.
(22) The glucose dehydrogenase according to (21), wherein the protein is a protein defined in the following (A) or (B) defined in the following (A) or (B):
(A) a protein which has the amino acid sequence of SEQ ID NO: 3;
(B) a protein which has the amino acid sequence of SEQ ID NO: 3 including substitution, deletion, insertion or addition of one or several amino acid residues and a glucose dehydrogenase activity.
(23) A protein defined in the following (A) or (B):
(A) a protein which has the amino acid sequence of SEQ ID NO: 3;
(B) a protein which has the amino acid sequence of SEQ ID NO: 3 including substitution, deletion, insertion or addition of one or several amino acid residues and a glucose dehydrogenase activity.
(24) A DNA encoding a protein defined in the following (A) or (B):
(A) a protein which has the amino acid sequence of SEQ ID NO: 3;
(B) a protein which has the amino acid sequence of SEQ ID NO: 3 including substitution, deletion, insertion or addition of one or several amino acid residues and a glucose dehydrogenase activity.
(25) The DNA according to (24), which is a DNA defined in the following (a) or (b):
(a) a DNA which comprises the nucleotide sequence of the nucleotide numbers 764 to 2380 in the nucleotide sequence of SEQ ID NO: 1;
(b) a DNA which is hybridizable with a nucleotide sequence comprising the sequence of the nucleotide numbers 764 to 2380 in SEQ ID NO: 1 or a probe that can be prepared from the sequence under a stringent condition and encodes a protein having a glucose dehydrogenase activity.
(26) A recombinant vector comprising the DNA according to (24) or (25).
(27) The recombinant vector according to (26), which comprises nucleotide sequences encoding the signal peptide according to (18) and a β-subunit.

(28) A transformant transformed with the DNA according to (24) or (25) or the recombinant vector according to (26) or (27).
(29) A method for producing glucose dehydrogenase comprising the steps of culturing the transformant according to (28) to produce glucose dehydrogenase as an expression product of the DNA, and collecting it.
(30) A *Burkhorderia cepacia* KS1 strain (FERM BP-7306).
(31) A glucose sensor using an enzyme electrode including the glucose dehydrogenase according to any one of (6) to (14), the protein according to any one of (20) to (23), the transformant according to (27) or the strain according to (30).
(32) A glucose assay kit including the glucose dehydrogenase according to any one of (6) to (14) or the protein according to any one of (20) to (23).
(33) A protein having the amino acid sequence of SEQ ID NO: 2.
(34) A DNA encoding a protein having the amino acid sequence of SEQ ID NO: 2.
(35) The DNA according to (34), which comprises the nucleotide sequence of the nucleotide numbers 258 to 761 in the nucleotide sequence of SEQ ID NO: 1.
(36) A DNA comprising the DNA according to (34) or (35) and the DNA according to (24) or (25) in this order.
(37) The DNA according to (36), which comprises the nucleotide sequence of the nucleotide numbers 258 to 2380 in the nucleotide sequence of SEQ ID NO: 1.
(38) A recombinant vector comprising the DNA according to (36) or (37).
(39) The recombinant vector according to (38), which comprises nucleotide sequences encoding the signal peptide according to (18) and a β-subunit.
(40) A transformant transformed with the DNA according to (36) or (37) or the recombinant vector according to (38) or (39).
(41) A method for producing glucose dehydrogenase comprising the steps of culturing the transformant according to (40) to produce glucose dehydrogenase as an expression substance of the DNA according to (36) or (37), and collecting it.

Hereafter, the present invention will be explained in detail.

<1> Novel Bacterial Strain Producing Glucose Dehydrogenase of the Present Invention The enzyme of the present invention (hereinafter, also referred to as "the enzyme" or "GDH") can be produced by a bacterium belonging to the genus *Burkhorderia*. The *Burkhorderia* bacterium used for the present invention is not particularly limited so long as it is a *Burkhorderia* bacterium having ability to produce the enzyme. However, *Burkhorderia cepacia*, in particular, the *Burkhorderia cepacia* KS1 strain is preferred. This bacterial strain is a novel bacterial strain isolated by the inventors of the present invention from soil near hot springs as described later in the examples and was identified as *Burkhorderia cepacia* based on its bacteriological properties. Conventionally, it has been unknown that a microorganism belonging to the genus *Burkhorderia* can produce glucose dehydrogenase. This bacterial strain was designated as KS1 strain. This strain was deposited at International Patent Organism Depositary, National Institute of Advanced Industrial Science and Technology (Tsukuba Central 6, 1-1, Higashi 1-chome, Tsukuba-shi, Ibaraki-ken, Japan, postal code: 305-8566) on Sep. 25, 2000 and received a microorganism accession number of FERM BP-7306.

The inventors of the present invention obtained some *Burkhorderia cepacia* strains other than the *Burkhorderia cepacia* KS1 strain, which were deposited at Institute for Fermentation (Osaka, IFO) or Japan Collection of Microorganisms (JCM), the Institute of Physical and Chemical Research, and measured their glucose dehydrogenase activities. As a result, they confirmed that all of these bacterial strains had the activity.

<2> Glucose Dehydrogenase of the Present Invention

If a *Burkhorderia* bacterium having glucose dehydrogenase producing ability, for example, the *Burkhorderia cepacia* KS1 strain, is cultured in a nutrient medium used for usual culture of a microorganism, preferably a medium containing glucose or a substance containing glucose in order to increase the enzyme producing ability, the glucose dehydrogenase of the present invention is produced and accumulated in a culture product or cultured cells. Therefore, it can be collected by a known method. The method for producing the enzyme will be specifically explained by exemplifying the *Burkhorderia cepacia* KS1 strain. First, the *Burkhorderia cepacia* KS1 strain is cultured in a suitable nutrient medium, for example, a medium containing suitable carbon source, nitrogen source, inorganic salts, glucose or substances containing these and so forth to produce and accumulate the enzyme in the culture product or the cultured cells.

As the carbon sources, any substance that can be assimilated can be used, and examples include, for example, D-glucose, L-arabinose, D-xylose, D-mannose, starch, various peptones and so forth. As the nitrogen sources, there can be used yeast extract, malt extract, various peptones, various meat extracts, corn steep liquor, amino acid solutions and organic and inorganic nitrogen compounds such as ammonium salts or substances containing these. As the inorganic salts, there can be used various phosphoric acid salts and salts of magnesium, potassium, sodium, calcium and so forth. Further, as required, various inorganic and organic substances required for growth of the bacterium or production of the enzyme, for example, silicone oil, sesame oil, defoaming agents such as various surfactants and vitamins can be added to the medium.

As for the culture method, although either liquid culture or solid culture may be used, liquid culture is usually preferred.

The enzyme of the present invention can be obtained from the medium and/or the cells in the culture obtained as described above. The enzyme existing in the cells can be obtained as a cell extract by disrupting or lysing the cells.

The glucose dehydrogenase in the culture product or the cell extract can be purified by a suitable combination of chromatography techniques using an ion exchanger, a gel filtration carrier, a hydrophobic carrier and so forth.

The activity of the enzyme can be measured by the same methods as known methods for measurement of the glucose dehydrogenase activity. Specifically, the activity can be measured by, for example, the method described later in the examples.

Physicochemical properties of the novel glucose dehydrogenase of the present invention are as follows:

(i) the enzyme has an action of catalyzing dehydrogenation reaction of glucose;

(ii) the enzyme consists of subunits showing a molecular weight of about 60 kDa and a molecular weight of about 43 kDa in SDS-polyacrylamide gel electrophoresis under a reducing condition;

(iii) the enzyme shows a molecular weight of about 380 kDa in gel filtration chromatography using TSK Gel G3000SW (Tosoh Corporation); and (iv) the enzyme shows an optimal reaction temperature around 45° C. (Tris-HCl buffer, pH 8.0).

The glucose dehydrogenase shows an activity peak around 45° C. under the aforementioned condition, and also shows an activity peak around 75° C. (refer to FIG. 3 (*a*)). No GDH has been known which shows the activity peak in two of temperature regions as described above.

The molecular weight and the optimal temperature can be measured by the methods described later in the examples.

The aforementioned glucose dehydrogenase of the present invention consists of two of separate polypeptides, the α-subunit having a molecular weight of about 60 kDa and the β-subunit having a molecular weight of about 43 kDa (hereinafter, this glucose dehydrogenase is also referred to as "multimer enzyme"). The inventors of the present invention further investigated these two of subunits in detail.

It was found that the β-subunit was cytochrome C (as shown later in the examples). A protein containing only the α-subunit exhibits the following physicochemical properties:
  (i) the protein can constitute the glucose dehydrogenase as a subunit;
  (ii) the protein has a glucose dehydrogenase activity;
  (iii) the protein shows a molecular weight of about 60 kDa in SDS-polyacrylamide gel electrophoresis under a reducing condition; and
  (iv) the protein shows an optimal reaction temperature around 75° C. (Tris-HCl buffer, pH 8.0).

The optimal temperature can be measured by the method described later in the examples.

Since this protein itself has the enzymatic activity, the protein may be optionally called as "peptide enzyme" or "enzyme" depending on the content of the explanation.

As a specific embodiment of the peptide enzyme of the present invention, a protein having the amino acid sequence of SEQ ID NO: 3 can be mentioned. Further, this peptide enzyme may be a protein having the amino acid sequence containing substitution, deletion, insertion or addition of one or more amino acid residues in the amino acid sequence of SEQ ID NO: 3 so long as it has the GDH activity. Although an amino acid sequence that can be encoded by the nucleotide sequence of SEQ ID NO: 1 is shown as SEQ ID NO: 3, the methionine residue at the N-terminus may be eliminated after translation.

Further, as a specific embodiment of the multimer enzyme of the present invention, there can be mentioned a multimer containing a protein of which α-subunit has the amino acid sequence of SEQ ID NO: 3. Further, the aforementioned multimer enzyme may be a multimer containing a protein of which α-subunit has the amino acid sequence of SEQ ID NO: 3 including substitution, deletion, insertion or addition of one or more amino acid residues, so long as it has the GDH activity.

In the present invention, "one or more" means a number of 1 to 10, preferably 1 to 5, particularly preferably 1 to 3.

The inventors of the present invention confirmed existence of a γ-subunit in addition to the aforementioned α-subunit and β-subunit.

In the examples described later, the γ-subunit was removed at the stage of purifying the enzyme of the present invention from a culture supernatant or cell extract, and therefore the γ-subunit was not confirmed in the purified enzyme. However, as shown in the examples, when the γ-subunit was expressed together with the α-subunit, a high enzymatic activity was obtained in comparison with the case where only the α-subunit was expressed. This suggested that the γ-subunit was a protein involved in the production of the α-subunit in a microbial cell in some sort of way. Assuming that the specific activity of the α-subunit (enzymatic activity per protein) is the same in either case, a lower enzymatic activity indicates a smaller amount of the α-subunit as an enzyme since the enzymatic activity reflects the amount of the enzyme. On the other hand, the produced α-subunit may be protected by the γ-subunit in a certain manner, or although the α-subunit as a protein is fully expressed, it cannot have the three-dimensional structure for exhibiting the enzymatic activity due to the absence of γ-subunit, and thus the enzymatic activity may become low. In either case, a high enzymatic activity can be obtained when the γ-subunit is expressed together with the α-subunit.

<3> DNA of the Present Invention

The DNA of the present invention can be obtained from a microorganism containing the DNA of the present invention, for example, *Burkhorderia cepacia*. The DNA of the present invention was isolated from chromosomal DNA of *Burkhorderia cepacia* in the process of accomplishing the present invention. However, since its nucleotide sequence and the amino acid sequence encoded by this nucleotide sequence were elucidated by the present invention, the DNA can also be obtained by chemical synthesis based on those sequences. Further, the DNA of the present invention can also be obtained from chromosomal DNA of *Burkhorderia cepacia* or the like by hybridization or PCR using an oligonucleotide prepared based on the aforementioned sequences as a probe or a primer.

In addition to a DNA which encodes a protein having the amino acid sequence of SEQ ID NO: 3, the DNA of the present invention may be a DNA which encodes a protein having an amino acid sequence of SEQ ID NO: 3 containing substitution, deletion, insertion or addition of one or more amino acid residues in the amino acid sequence and has the GDH activity.

As the DNA of the present invention, there can be specifically mentioned a DNA comprising the nucleotide sequence of the nucleotide numbers 764 to 2380 in the nucleotide sequence of SEQ ID NO: 1. The nucleotide sequence of the nucleotide numbers 764 to 2380 in the nucleotide sequence of SEQ ID NO: 1 encodes the α-subunit of GDH having the amino acid sequence of SEQ ID NO: 3.

Further, the DNA of the present invention may also be a DNA which is hybridizable with the nucleotide sequence of the nucleotide numbers 764 to 2380 in the nucleotide sequence of SEQ ID NO: 1 or a probe that can be prepared from the sequence under a stringent conditions and encodes a protein having the GDH activity.

It is estimated that the nucleotide sequence of the nucleotide numbers 258 to 761 in the nucleotide sequence of SEQ ID NO: 1 encodes the γ-subunit. The amino acid sequence is shown in SEQ ID NO: 2. It is considered that, since the structural gene of the γ-subunit is included in a region upstream from that of the α-subunit, and thus the γ-subunit is expressed first and already exists as a protein upon the production of the α-subunit by a microorganism, the α-subunit can be efficiently produced in the microorganism. Therefore, the DNA of the present invention may include a DNA encoding the amino acid sequence of SEQ ID NO: 2 in addition to the aforementioned DNA.

A DNA encoding a protein substantially identical to the aforementioned protein having the amino acid sequence of SEQ ID NO: 3 can be obtained by, for example, a method such as the site-directed mutagenesis or mutagenesis treatment. The GDH activity of a protein encoded by a DNA introduced with a mutation can be measured, for example, as follows.

An enzyme sample and glucose as a substrate are added to 10 mM potassium phosphate buffer (pH 7.0) containing 594 μM methylphenazine methosulfate (mPMS) and 5.94 μM 2,6-dichlorophenol-indophenol (DCIP) and incubated at 37° C. Change in absorbance of the DCIP at 600 nm is monitored by using a spectrophotometer, and the absorbance decreasing rate is measured as an enzymatic reaction rate.

Further, the nucleotide sequence consisting of the nucleotide of the nucleotide number 2386 and the sequence after the nucleotide of the nucleotide number 2386 in the nucleotide sequence of SEQ ID NO: 1 is estimated to encode the β-subunit. Further, the nucleotide sequence of the nucleotide numbers 2386 to 2451 is estimated to encode the signal peptide of the β-subunit. An estimated amino acid sequence of this signal peptide is the amino acid sequence of amino acid numbers 1 to 22 in SEQ ID NO: 4. The signal peptide is a peptide necessary for a protein synthesized in ribosome to be secreted through the membrane and has been found to comprise 15 to 30 hydrophobic amino acid residues. Therefore, since the amount of proteins in the culture supernatant is increased due to the existence of the signal peptide, this is a peptide effectively acting in a method of producing a protein.

Hereafter, an example of a method for obtaining the DNA of the present invention will be explained.

Chromosomal DNA is isolated from a microorganism such as *Burkholderia cepacia* and purified, and the chromosomal DNA is cleaved by ultrasonication, restriction enzyme treatment or the like and ligated to a linear expression vector and cyclized by using a DNA ligase or the like to construct a recombinant vector. The obtained recombinant vector is introduced into a host microorganism in which the vector is autonomously replicable, and the transformants are screened by using a vector marker and expression of an enzymatic activity as indexes to obtain a microorganism harboring a recombinant vector containing a gene encoding GDH. The recombinant vector contained in the obtained microorganism is expected to contain at least the nucleotide sequence encoding the α-subunit. Further, if the cloned fragment has a sufficient size, it is very likely that the nucleotide sequence encoding the γ-subunit is also contained.

Then, the microorganism having the recombinant vector can be cultured, the recombinant vector can be isolated from the cells of the cultured microorganism and purified, and the gene encoding GDH can be collected from the expression vector. For example, chromosomal DNA serving as a gene donor is specifically collected, for example, as follows.

The aforementioned gene donor microorganism can be cultured with stirring for 1 to 3 days, for example, and cells can be collected by centrifugation from the obtained culture broth and then lysed to prepare cell lysate containing the GDH gene. As the method for lysis of the cells, a treatment is performed by using a bacteriolytic enzyme such as lysozyme, and other enzymes such as protease and surfactants such as sodium dodecylsulfate (SDS) are used in combination as required. Further, a physical cell disruption method such as freeze and thawing or French press treatment may also be employed in combination.

The DNA can be isolated and purified from the lysate obtained as described above in a conventional manner, for example, by a suitable combination of deproteinization by phenol treatment or protease treatment, ribonuclease treatment, alcohol precipitation and so forth.

The DNA isolated and purified from a microorganism can be cleaved by, for example, ultrasonication, restriction enzyme treatment or the like. Preferably, a type-II restriction enzyme, which acts on a specific nucleotide sequence, is suitably used. The restriction enzyme used may generate an end matching a digested end of a vector, or the digested end may be blunt-ended by using an arbitrary restriction enzyme and ligated to the vector.

As the vector used for cloning, a phage that can autonomously grow in a host microorganism or a plasmid that is constructed for gene recombination is suitable. Examples of the phage include, for example, when *Escherichia coli* is used as the host microorganism, Lambda gt10, Lambda gt11 and so forth. Further, examples of the plasmid include, for example, when *Escherichia coli* is used as the host microorganism, pBR322, pUC18, pUC118, pUC19, pUC119, pTrc99A and pBluescript as well as SuperCosI, which is a cosmid, and so forth.

Upon the cloning, a vector fragment can be obtained by digesting the aforementioned vector with a restriction enzyme used for the digestion of a microbial DNA as the aforementioned donor of a gene encoding GDH. However, a restriction enzyme identical to the restriction enzyme used for the digestion of the microbial DNA does not necessarily need to be used. The method for ligating the microbial DNA fragment and the vector DNA fragment may be a known method using a DNA ligase. For example, an adhesive end of the microbial DNA fragment and an adhesive end of the vector fragment are ligated, and then a recombinant vector containing the microbial DNA fragment and the vector DNA fragment is produced by using a suitable DNA ligase. If required, after the ligation, the fragment can also be introduced into the host microorganism to produce the recombinant vector by utilizing a DNA ligase existing in the microorganism.

The host microorganism used for the cloning is not particularly limited so long as the recombinant vector is stable and can autonomously grow in the host, and a foreign gene can be expressed in the host. *Escherichia coli* DH5α, XL-1 BlueMR and so forth can generally be used.

As the method for introducing the recombinant vector into the host microorganism, for example, when the host microorganism is *Escherichia coli*, the competent cell method using calcium treatment, electroporation or the like can be used.

Whether the cloned fragment obtained by the aforementioned method encodes GDH can be confirmed by decoding the nucleotide sequence of the fragment in a conventional manner.

The DNA of the present invention can be obtained by collecting a recombinant vector from the transformant obtained as described above.

GDH can be produced by culturing a transformant containing the DNA of the present invention or a recombinant vector containing the DNA to produce GDH as an expression product of the DNA and collecting it from the cells or culture broth. For this production, although the DNA of the present invention may be a DNA encoding the α-subunit, the expression efficiency can be increased by further expressing the γ-subunit together with the α-subunit.

Examples of the microorganism in which GDH is produced include enteric bacteria such as *Escherichia coli*, Gram-negative bacteria such as those of the genera *Pseudomonas* and *Gluconobacter*, Gram-positive bacteria including *Bacillus* bacteria such as *Bacillus subtilis*, yeasts such as *Saccharomyces cerevisiae* and filamentous fungi such as *Aspergillus niger*. However, the microorganism is not limited to these microorganisms, and any host microorganism suitable for production of foreign proteins can be used.

The GDH gene contained in the once selected recombinant vector containing the GDH gene can be easily transferred into a recombinant vector that can be replicated in a microorganism by recovering a DNA which is the GDH gene from the recombinant vector containing the GDH gene by using a restriction enzyme or by PCR and ligating it to another vector fragment. Further, the microorganism can be easily transformed with these vectors, for example, by the competent cell method using calcium treatment for *Escherichia* bacteria, the protoplast method for *Bacillus* bacteria, the KU or KUR method for yeasts, the micromanipulation method for filamentous fungi and so forth. Further, electroporation can also be widely used.

The host microorganism into which a target recombinant vector is introduced can be selected by searching a microorganism that simultaneously expresses a drug resistance marker of the vector containing the target DNA and the GDH activity. For example, a microorganism growing in a selective medium based on the drug resistance marker and producing GDH can be selected.

As for the culture method of the transformant, culture conditions can be selected by considering nutritional and physiological properties of the host. In many cases, liquid culture is performed. It is industrially advantageous to perform aerobic culture with stirring.

As nutrients of the medium, those usually used for culture of microorganisms can be widely used. As carbon sources, any carbon compounds that can be assimilated can be used, and examples thereof include glucose, sucrose, lactose, maltose, lactose, molasses, pyruvic acid and so forth. Further, as nitrogen sources, any nitrogen compounds that can be utilized can be used, and examples thereof include peptone, meat extracts, yeast extract, casein hydrolysate, soybean meal alkaline extract and so forth. In addition, phosphoric acid salts, carbonic acid salts, sulfuric acid salts, salts of magnesium, calcium, potassium, iron, manganese, zinc and so forth, particular amino acids, particular vitamins and so forth are used as required.

Although the culture temperature can be appropriately changed in a range in which bacteria grow and produce GDH, it is preferably about 20° C. to 42° C. The culture time somewhat varies depending on the conditions. However, the culture can be completed at an appropriate time estimated to give the maximum GDH level, and the culture time is usually about 12 to 72 hours. Although pH of the medium can be appropriately changed in a range in which bacteria grow and produce GDH, it is preferably in the range of about pH 6.0 to 9.0.

The culture broth containing cells producing GDH in the culture can be collected and utilized as they are. However, when GDH exists in the culture broth, the culture broth is usually separated into a GDH-containing solution and microorganism cells by filtration, centrifugation or the like in a conventional manner and then used. When GDH exists in the cells, the cells are collected from the obtained culture by means of filtration, centrifugation or the like, and then the cells are disrupted by a mechanical method or an enzymatic method such as use of lysozyme, and further added with a chelating agent such as EDTA and a surfactant to solubilize GDH, as required, to isolate and collect GHD as an aqueous solution.

GDH can be precipitated from the GDH-containing solution obtained as described above by, for example, vacuum concentration, membrane concentration, salting out with ammonium sulfate, sodium sulfate or the like, or a fractional precipitation with a hydrophilic organic solvent such as methanol, ethanol and acetone. Further, heat treatment and isoelectric point treatment are also effective purification means. Then, GDH can be purified by a suitable combination of gel filtration using an adsorbent or gel filtration agent, absorption chromatography, ion exchange chromatography and affinity chromatography to obtain purified GHD.

A purified enzyme preparation can be obtained by isolation and purification based on column chromatography. Although the purified enzyme preparation is preferably purified to such an extent that a single band should be obtained in electrophoresis (SDS-PAGE), it may contain the γ-subunit.

The purified enzyme obtained as described above can be made into powder by, for example, lyophilization, vacuum drying, spray drying or the like and distributed.

Further, the amino acid sequence of the β-subunit can also be determined in the same manner as in the determination of the amino acid sequence of the α-subunit described later in the examples, and a DNA encoding the β-subunit can be isolated based on the sequence. Further, the β-subunit can also be produced by using the obtained DNA. Further, the multimer enzyme can also be produced by using a DNA encoding the α-subunit and DNA encoding the β-subunit.

<4> Glucose Sensor of the Present Invention

The glucose sensor of the present invention is characterized by using the enzyme of the present invention (the aforementioned multimer enzyme or peptide enzyme, or the aforementioned multimer enzyme or peptide enzyme containing the γ-subunit), the transformant of the present invention, or the microorganism of the present invention (*Burkhorderia cepacia* KS1 strain) as an enzyme electrode. As the electrode, a carbon electrode, gold electrode, platinum electrode or the like can be used, and the enzyme of the present invention is immobilized on this electrode. Examples of the method for immobilization include a method of using a crosslinking reagent, a method of entrapping the enzyme in a polymer matrix, a method of covering the enzyme with a dialysis membrane, methods of using a photocrosslinking polymer, conductive polymer, oxidation-reduction polymer or the like. Alternatively, the enzyme may be immobilized in a polymer or immobilized on an electrode by adsorption together with an electronic mediator of which typical examples are ferrocene and derivatives thereof, or these methods may be used in combination. Typically, the glucose dehydrogenase of the present invention is immobilized on a carbon electrode by using glutaraldehyde, and glutaraldehyde is blocked by a treatment with a reagent having an amine group.

The glucose concentration can be measured as follows. A buffer is placed in a constant temperature cell and added with a mediator, and a constant temperature is maintained. As the mediator, potassium ferricyanide, phenazine methosulfate and for forth can be used. An electrode on which the enzyme of the present invention is immobilized is used as a working electrode, and a counter electrode (e.g., platinum electrode) and a reference electrode (e.g., Ag/AgC electrode) are used. A constant voltage is applied to the carbon electrode, and after a steady-state current is obtained, a sample containing glucose is added and the increase of the current is measured. The glucose concentration in the sample can be calculated according to a calibration curve produced by using glucose solutions having standard concentrations.

<5> Glucose Assay Kit of the Present Invention

The saccharide assay kit of the present invention is characterized by including the enzyme of the present invention (the aforementioned multimer enzyme or peptide enzyme, or the aforementioned multimer enzyme or peptide enzyme containing the γ-subunit). The glucose assay kit of the present invention includes the enzyme of the present invention in an amount sufficient for at least one assay. Typically, the kit includes, in addition to the enzyme of the present invention, a buffer, a mediator, standard solutions of glucose or the like for creating a calibration curve, which are necessary for the assay, and a guideline for use. The enzyme of the present invention can be provided in various forms, for example, as a lyophilized reagent or a solution in an appropriate storage solution.

BEST MODE FOR CARRYING OUT THE INVENTION

Figure 1:
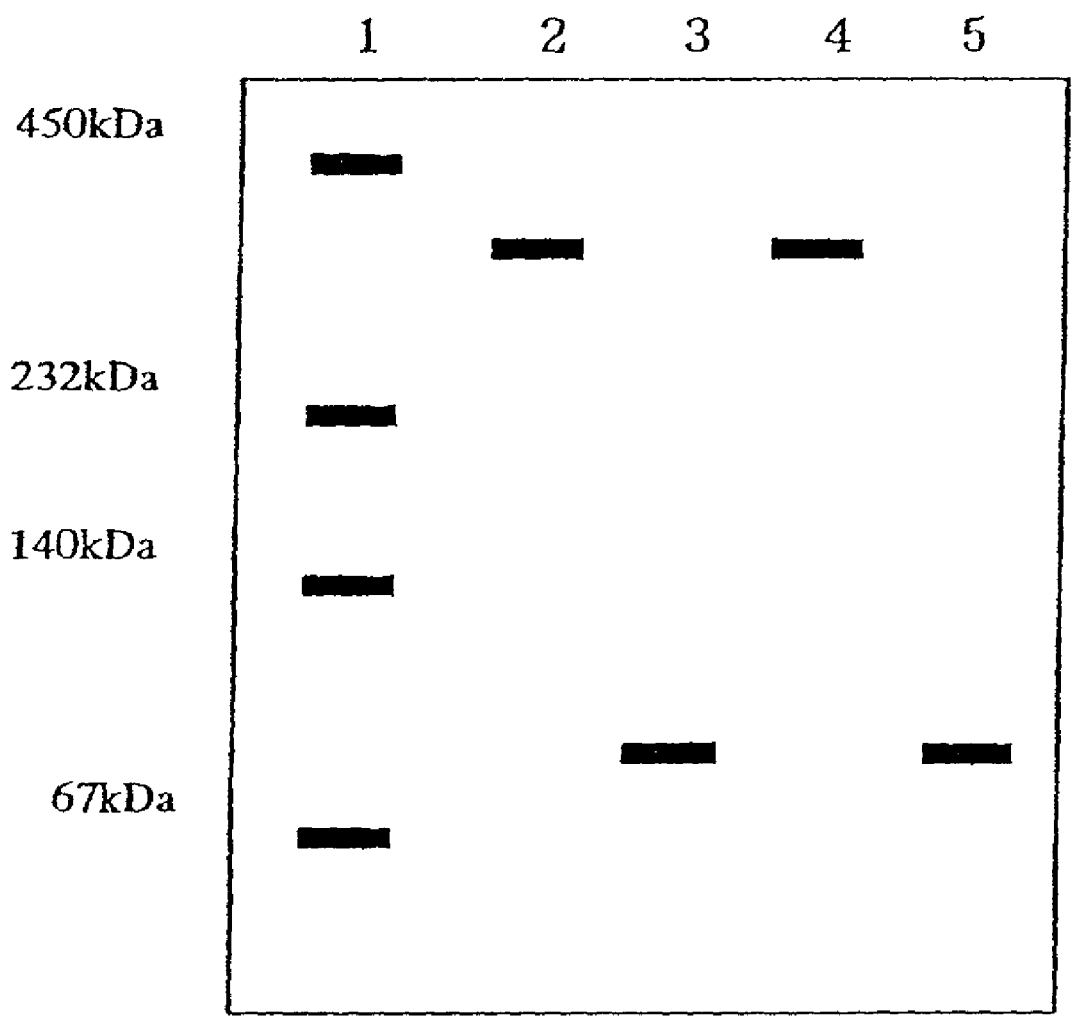
FIG. 1 shows a molecular weight of the enzyme of the present invention determined by native PAGE electrophoresis.

The present invention will be explained more specifically with reference to the following examples.

Example 1

Acquisition of Bacterium Having Glucose Dehydrogenase Producing Ability

[Screening]

The microorganism of the present invention was obtained by collecting soil near various hot springs in Japan and selecting a bacterium having a glucose dehydrogenase activity among bacteria utilizing glucose as a nutrient from the soil.

The results of investigation of morphological characteristics, growth characteristics and physiological characteristics of this strain are shown below.

[Bacteriological Characteristics]

| | |
|---|---|
| Gram staining | negative |
| Cell morphology | rod-shaped |
| With polar flagellum | |
| Mobility | positive |
| Number of fragments | >5 |
| Optimal growth temperature | 45° C. |
| Oxidase | negative |
| Catalase | positive |
| Production of acetoin | negative |
| Production of H$_2$S | negative |
| Production of indole | negative |
| Acid from glucose | positive |
| Arginine dihydrolase | negative |
| Urease | negative |
| β-Glucosidase | negative |
| Protease | negative |
| β-Galactosidase | positive |
| Lysine carboxylase | negative |
| Ornithine carboxylase | negative |
| Reduction of nitrate | positive |

[Assimilation Characteristics]

| | |
|---|---|
| Glycerol | positive |
| Erythritol | negative |
| D-Arabinose | negative |
| L-Arabinose | positive |
| Ribose | positive |
| D-Xylose | positive |
| L-Xylose | negative |
| Adonitol | positive |
| β-Methyl-xyloside | negative |
| Galactose | positive |
| D-Glucose | positive |
| D-Fructose | positive |
| D-Mannose | positive |
| L-Sorbose | negative |
| Rhamnose | negative |
| Dulcitol | positive |
| Inositol | positive |
| Mannitol | positive |
| Sorbitol | positive |
| α-Methyl-D-mannoside | negative |
| α-Methyl-D-glucoside | negative |
| N-Acetyl-glucosamine | positive |
| Amygdaline | negative |
| Arbutin | negative |
| Esculin | negative |
| Salicin | negative |
| Cellobiose | negative |
| Maltose | negative |
| Lactose | negative |
| Melibiose | negative |
| Sucrose | negative |
| Trehalose | positive |
| Inulin | negative |
| Melezitose | negative |
| D-Raffinose | negative |
| Amidon | negative |
| Glycogen | negative |
| Xylitol | positive |
| β-Gentiobiose | negative |
| D-Turanose | negative |
| D-Lyxose | negative |
| D-Tagatose | negative |
| D-Fucose | negative |
| L-Fucose | negative |
| D-Arabitol | positive |
| L-Arabitol | positive |
| Gluconic acid | positive |
| 2-Ketogluconic acid | positive |
| 5-Ketogluconic acid | negative |
| Capric acid | positive |
| Adipic acid | positive |
| Malic acid | positive |
| Citric acid | positive |
| Phenyl acetate | positive |

[Oxidation Characteristics]

| | |
|---|---|
| Glycerol | negative |
| Erythritol | negative |
| D-Arabinose | negative |
| L-Arabinose | positive |
| Ribose | positive |
| D-Xylose | positive |
| L-Xylose | negative |
| Adonitol | positive |
| β-Methyl-xyloside | negative |
| Galactose | positive |
| D-Glucose | positive |
| D-Fructose | positive |
| D-Mannose | positive |
| L-Sorbose | negative |
| Rhamnose | negative |
| Dulcitol | positive |
| Inositol | positive |
| Mannitol | positive |
| Sorbitol | positive |
| α-Methyl-D-mannoside | negative |
| α-Methyl-D-glucoside | negative |
| N-Acetyl-glucosamine | negative |
| Amygdaline | negative |
| Arbutin | negative |
| Esculin | positive |
| Salicin | negative |
| Cellobiose | positive |
| Maltose | positive |
| Lactose | positive |

| | |
|---|---|
| Melibiose | negative |
| Sucrose | negative |
| Trehalose | positive |
| Inulin | negative |
| Melezitose | negative |
| D-Raffinose | negative |
| Amidon | negative |
| Glycogen | negative |
| Xylitol | negative |
| β-Gentiobiose | positive |
| D-Turanose | negative |
| D-Lyxose | negative |
| D-Tagatose | negative |
| D-Fucose | positive |
| L-Fucose | negative |
| D-Arabitol | positive |
| L-Arabitol | positive |
| Gluconic acid | negative |
| 2-Ketogluconic acid | negative |
| 5-Ketogluconic acid | negative |

The taxonomical position of the KS1 strain having the aforementioned bacteriological characteristics was investigated with reference to the Bergey's Manual of Determinative Bacteriology, and the strain was identified to belong to the genus Burkhorderia, and was a bacterial strain of Burkhorderia cepacia.

The genus Burkhorderia was conventionally classified into the genus Pseudomonas, but is separately classified as the genus Burkhorderia at present (Yabuuchi, E., Kosako, Y., Oyaizu, H., Yano, I., Hotta, H., Hashimoto, Y., Ezaki, T. and Arakawa, M., Microbiol. Immunol. Vol. 36 (12): 1251-1275 (1992); International Journal of Systematic Bacteriology, Apr., 1993, pp. 398-399).

Further, the inventors of the present invention obtained several Burkhorderia cepacia strains other than the Burkhorderia cepacia KS1 strain, which were deposited at the Institute for Fermentation, Osaka or the Japan Collection of Microorganisms (JCM), Institute of Physical and Chemical Research, and measured glucose dehydrogenase activities of the strains, and they were confirmed to have the activity. The glucose dehydrogenase activity was measured by the method described later in Example 2. Relative activities of these strains based on the enzymatic activity of a water-soluble fraction of the KS1 strain, which is taken as 100, are shown in Table 1.

TABLE 1

| Bacterial strain | | Glucose dehydrogenase activity | |
|---|---|---|---|
| | | 70° C. | 45° C. |
| KS1 | Water-soluble fraction | 100 | 100 |
| JCM5506 | Water-soluble fraction | 100 | 100 |
| | Membrane fraction | 100 | 100 |
| JCM5507 | Water-soluble fraction | 100 | 100 |
| | Membrane fraction | 100 | 100 |
| JCM2800 | Water-soluble fraction | 100 | 100 |
| JCM2801 | Water-soluble fraction | 100 | 100 |
| IFO15124 | Water-soluble fraction | 100 | 100 |
| IFO14595 | Water-soluble fraction | 100 | 100 |

Example 2

Extraction of Glucose Dehydrogenase

<1> Culture of Cells

As the culture conditions of the bacterium, usual aerobic culture conditions were used. The cells were cultured at 34° C. for 8 hours in 7 L of a medium containing the following ingredients per liter.

| | |
|---|---|
| Polypeptone | 10 g |
| Yeast extract | 1 g |
| NaCl | 5 g |
| $KH_2PO_4$ | 2 g |
| Glucose | 5 g |
| Einol (ABLE Co., Tokyo, Japan) | 0.14 g |
| Total volume including distilled water | 1 L |
| Adjusted pH | 7.2 |

In a volume of 7 L of the culture broth was centrifuged at 9,000×g at 4° C. for 10 minutes to obtain about 60 g of cells.

<2> Preparation of Roughly Purified Fraction

In an amount of 60 g of the cells were dispersed in 10 mM potassium phosphate buffer (pH 6.0), and a pressure difference of 1,500 Kg/cm$^2$ was applied to the cells by using a French press (Otake Corporation, Tokyo, Japan) to disrupt cell membranes. The cell extract was centrifuged at 8000×g for 10 minutes to remove cellular solid. Further, the supernatant was subjected to ultracentrifugation at 69,800×g at 4° C. for 90 minutes to obtain about 8 g of a membrane fraction as precipitates.

<3> Purification of Enzyme

The membrane fraction was redispersed in 10 mM potassium phosphate buffer (pH 6.0) containing 1% of Triton X-100 as a final concentration. Then, the dispersion was slowly stirred overnight at 4° C. After the dispersion was subjected to ultracentrifugation (69,800×g, 4° C., 90 minutes), the solubilized membrane fraction was centrifuged again at 4° C. for 15 minutes at 15,000×g to obtain a supernatant.

The solubilized membrane fraction was added with the same volume of 10 mM potassium phosphate buffer (pH 8.0) containing 0.2% Triton X-100. The solution was dialyzed, and then applied to a DEAE-TOYOPEARL column (22 mm ID×20 cm, Tosoh Corporation, Tokyo, Japan) equalized with 10 mM potassium phosphate buffer (pH 8.0) containing 0.2% Triton X-100. Proteins were eluted with a linear gradient of 0 to 0.15 M NaCl in 10 mM potassium phosphate buffer (pH 8.0). The flow rate was 5 ml/min. GDH was eluted at a NaCl concentration of about 75 mM. Fractions exhibiting the GDH activity were collected and dialyzed overnight against 10 mM potassium phosphate buffer (pH 8.0, 4° C.) containing 0.2% Triton X-100.

Further, the dialyzed enzyme solution was applied to a DEAE-5PW column (8.0 mm ID×7.5 cm, Tosoh Corporation, Tokyo, Japan). This column was equilibrated beforehand with 10 mM potassium phosphate buffer (pH 6.0) containing 0.2% Triton X-100. The proteins were eluted with a linear gradient of 0 to 100 mM NaCl in 10 mM potassium phosphate buffer (pH 8.0). The flow rate was 1 ml/min. Fractions exhibiting the GDH activity were eluted at a NaCl concentration of about 20 mM. The fractions having the GDH activity were collected and desalted overnight with 10 mM potassium phosphate buffer (pH 8.0) containing 0.2% Triton X-100 to obtain the purified enzyme.

The GDH activity was measured according to the following method throughout this example and the following examples.

As electron acceptors, 2,6-dichlorophenol-indophenol (DCIP) and phenazine methosulfate (PMS) were used. The reaction was allowed in a polyethylene tube at a predetermined temperature. In a volume of 5 μl of the enzyme solution was added to 20 μl of 25 mM Tris-HCl buffer (pH 8.0) containing 0.75 mM PMS and 0.75 mM DCIP. This mixture was left for 1 minute beforehand at a constant temperature. The reaction was started with the addition of 1 μl of 2 M glucose (final concentration: 77 mM) and left at a constant temperature for 2 minutes. Subsequently, 100 μl of ice-cooled distilled water or 120 μl of 7.5 M urea was added to cool the sample. A reduction reaction of the electron acceptors due to the dehydrogenation of glucose was monitored by using an ultra-micro measurement cell (100 μl) and a spectrophotometer (UV160, Shimadzu Corporation, Kyoto, Japan) that enabled measurement using the cell. That is, decoloration with time due to the reduction of DCIP was measured at 600 nm, which is the absorption wavelength of DCIP. The molar absorbance coefficient of DCIP (22.23 mM×cm$^{-1}$) was used. One unit (U) of the enzyme was defined as the amount of oxidizing 1 μM of glucose per minute under standard test conditions. The protein concentration was measured by the Lowry method.

Example 3

Native PAGE electrophoresis was performed for the purified enzyme. The electrophoresis was performed on 8 to 25% polyacrylamide gradient gel using a Tris-alanine buffer system containing 1% Triton X-100. The gel was stained with silver nitrate. As protein markers, thyroglobulin (669 kDa), ferritin (440 kDa), catalase (232 kDa), aldolase (158 kDa), bovine serum albumin (67 kDa), ovalbumin (43 kDa) and chymotrypsinogen A (25 kDa) were used.

Further, activity staining was performed for the native PAGE gel by incubating the gel in the following solution for 30 minutes. At GDH activity sites, nitroblue tetrazolium was reduced and formazan was produced, resulting in development of dark purple color.

| | |
|---|---|
| 200 mM | glucose |
| 0.1 mM | nitroblue tetrazolium |
| 0.3 mM | phenazine methosulfate |
| 20 mM | Tris-HCl buffer (pH 8.0) |

From the results of the silver staining in the native PAGE, it was estimated that the enzyme consisted of a single kind of enzyme and had a molecular weight of about 400 kDa. Further, when the gel was stained for the activity, the activity was observed at a site of the same mobility as in the silver staining (See FIG. 1. In the figure, Lane 1 shows the results of silver staining of marker proteins having standard molecular weights, Lane 2 shows the silver staining of the enzyme, and Lane 4 shows the staining for activity of the enzyme). When the enzyme was heated at 70° C. for 30 minutes, the activity unexpectedly remained, and the enzyme was separated into proteins one of which had the activity and showed a molecular weight of about 85 kDa (See FIG. 1. In the figure, Lane 3 shows the results of the silver staining of the enzyme heated at 70° C. for 30 minutes, and Lane 5 shows the staining for activity of the enzyme heated at 70° C. for 30 minutes). These results suggest that the enzyme consists of subunits.

Example 4

Figure 2:
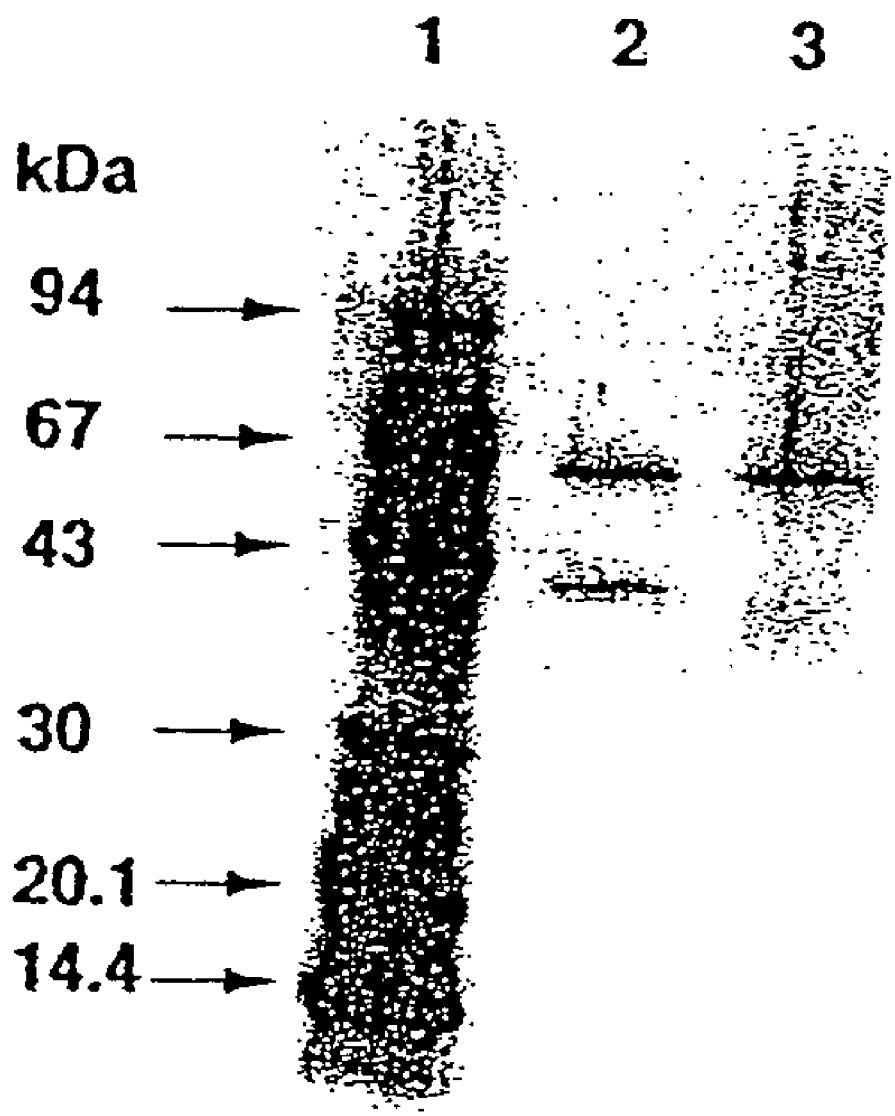
FIG. 2 shows an electrophoretic photograph showing a molecular weight of the enzyme of the present invention based on SDS-PAGE electrophoresis.

The purified enzyme solution was subjected to SDS-PAGE. SDS-PAGE was performed in 8 to 25% gradient polyacrylamide gel by using a Tris-tricine buffer. Proteins in the gel were stained with silver nitrate. Separation and development were automatically performed by using Phast System (Pharmacia). The molecular mass was determined based on the relative migrations of the standard proteins. The enzyme was separated into proteins having molecular weights of about 60 kDa and 43 kDa by SDS-PAGE (See FIG. 2. FIG. 2 is an electrophoretic photograph. In the figure, Lane 1 shows the results of the silver nitrate staining of the marker proteins having standard molecular weights, and Lane 2 shows the results of the silver nitrate staining of the enzyme). Thus, it was suggested that the α-subunit of 60 kDa and the β-subunit of 43 kDa were bound in the enzyme, and it was expected that an octamer was formed by four each of these subunits bonding to each other.

The β-subunit, a protein of 43 kDa separated by SDS-PAGE, was transferred onto a polyvinylidene fluoride membrane, and then the amino acid sequence at the N-terminus of the β-subunit was determined by using an amino acid sequencer (PPSQ-10, Shimadzu Corporation). As a result, it was found that the amino acid sequence at the N-terminus of the protein consisted of 16 residues of the amino acid sequence of SEQ ID NO: 5.

Further, the results obtained with the enzyme subjected to a heat treatment at 70° C. for 30 minutes are shown as Lane 3 in FIG. 2. Based on this result of SDS-PAGE, it can be estimated that the enzyme was changed into a single polypeptide having a molecular weight of 60 kDa after the heat treatment.

Example 5

The enzyme was subjected to gel filtration chromatography. As the gel, TSK Gel G3000SW (Tosoh Corporation) was used, and the gel column (8.0 mm ID×30 cm Tosoh Corporation, Tokyo, Japan) was equilibrated with a solution containing 0.3 M NaCl and 0.1% Triton X-100 in 10 mM potassium phosphate buffer (pH 6.0). Fractions (125 μl) were collected. Seven kinds of protein markers were used to determine the molecular weight of the purified enzyme. As the protein markers, thyroglobulin (669 kDa), ferritin (440 kDa), catalase (232 kDa), aldolase (158 kDa), bovine serum albumin (67 kDa), ovalbumin (43 kDa) and chymotrypsinogen A (25 kDa) were used.

It was confirmed that the molecular weight of the enzyme was about 380 kDa.

Example 6

The optimal temperature of the purified enzyme was examined.

Figure 3:
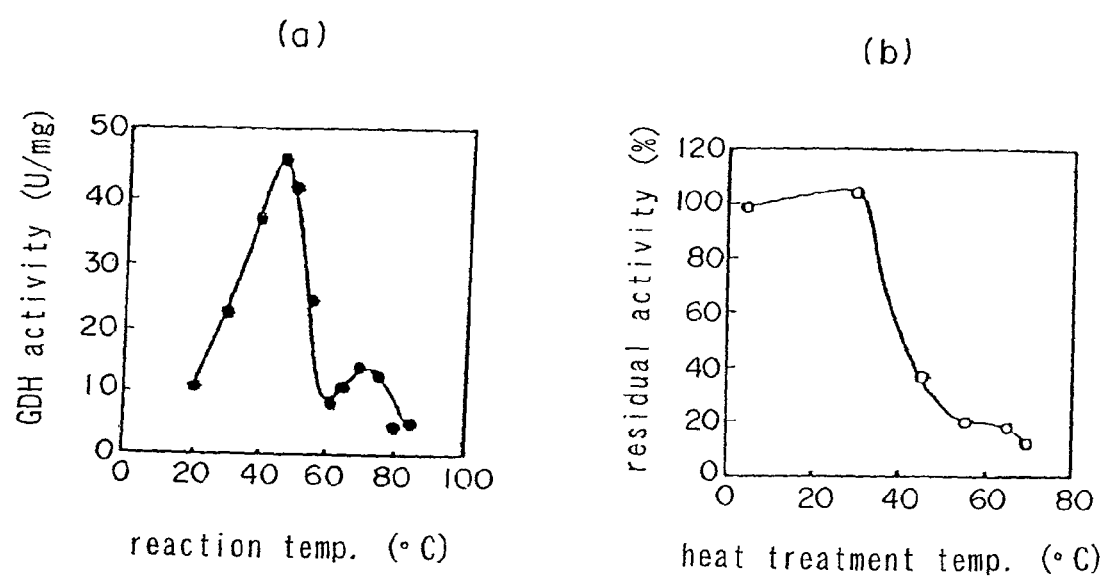
FIG. 3 shows the optimal reaction temperature (a) and thermal stability (b) of the enzyme of the present invention.

The enzyme was incubated beforehand in Tris-HCl buffer (pH 8.0) at a predetermined temperature for 1 minute, and then the reaction was started. The activity was measured at a predetermined reaction temperature. The optimal temperature was observed around 45° C. (see FIG. 3 (*a*)). Further, a peak was also observed around 75° C., although the activity was lower than the activity around 45° C.

Further, in order to examine thermal stability of the enzyme, the enzyme was left at each constant temperature for 30 minutes, and the residual enzymatic activity was measured at 45° C. (see FIG. 3 (b)).

Example 7

The optimal temperature and the thermal stability of the peptide enzyme constituting the single oligopeptide having a molecular weight of 60 kDa obtained by heating the enzyme at 70° C. for 30 minutes were examined.

This peptide enzyme showed an optimal temperature higher than that of the unheated enzyme as well as thermal stability. There has been no report about an enzyme having such temperature dependency.

Figure 4:
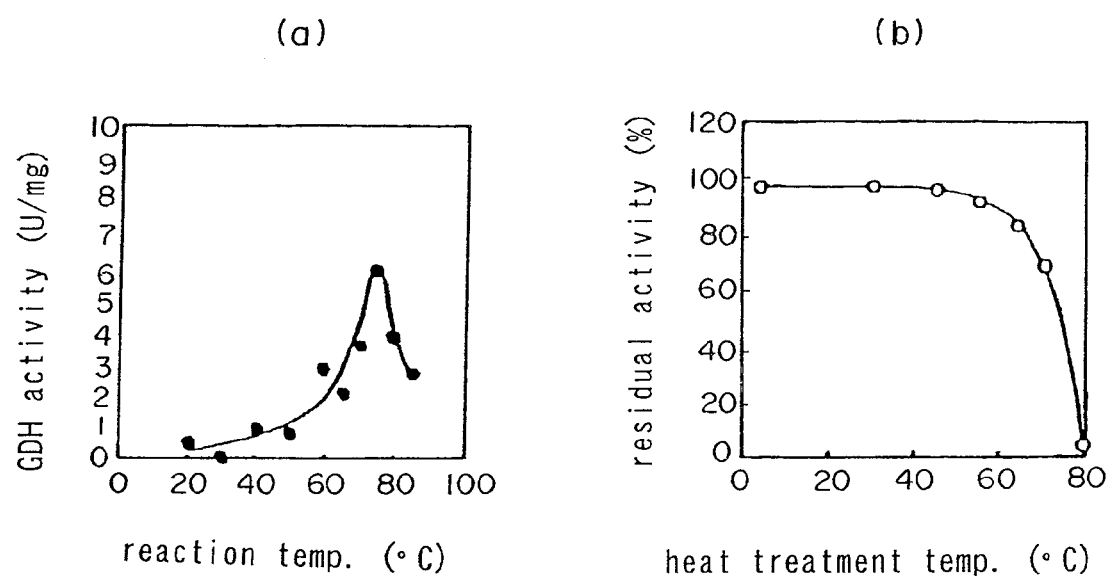
FIG. 4 shows the optimal reaction temperature (a) and thermal stability (b) of a peptide enzyme constituting only the α-subunit of the enzyme of the present invention.

The enzyme was incubated beforehand in Tris-HCl buffer (pH 8.0) at a predetermined temperature for 1 minute, and then the reaction was started. The activity was measured at a predetermined reaction temperature. The optimal temperature was observed around 75° C. (see FIG. 4 (a)).

Further, in order to examine thermal stability of the enzyme, the enzyme was left at each constant temperature for 30 minutes, and the residual enzymatic activity was measured at 70° C. (see FIG. 4 (b)).

Example 8

Figure 5:
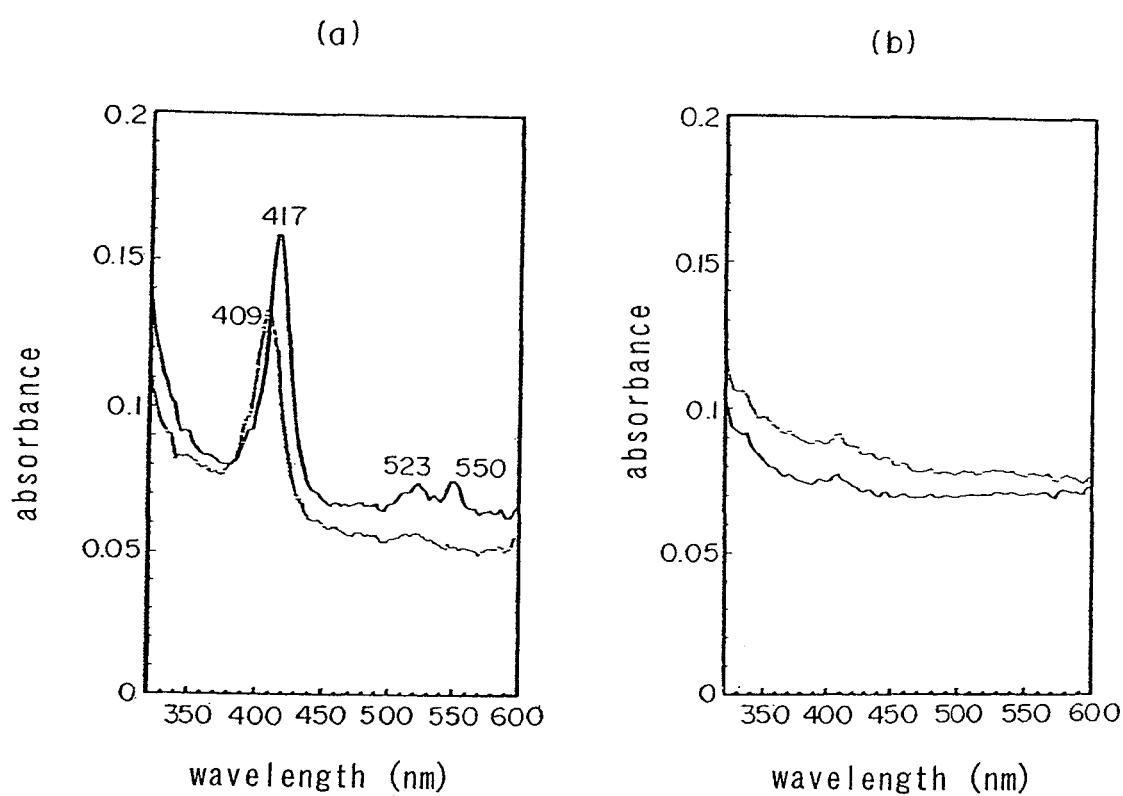
FIG. 5 shows results of spectrophotometric analyses of the enzyme of the present invention in the absence or presence of glucose before heat treatment (a) and spectrophotometric analyses of the enzyme of the present invention in the absence or presence of glucose after heat treatment (b).

In order to investigate a role of each subunit, spectrophotometric analysis was performed for GDH before and after the heat treatment. FIGS. 5 (a) and (b) show absorptions of oxidized and reduced GDHs before and after heat treatment (in the presence of glucose). The absorption wavelength of the oxidized GDH before heat treatment, which was the original GDH, showed a characteristic peak at 409 nm. Further, the peak shifted to 417 nm in the presence of glucose, and two more peaks were observed at 523 nm and 550 nm (FIG. 5 (a)). In contrast, the GDH after the heat treatment no longer showed the characteristic peak at 409 nm (FIG. 5 (b)), and no significant difference was observed between the oxidized and reduced GDHs.

The absorption wavelength of the oxidized GDH before heat treatment, which was the original GDH, was similar to the absorption wavelength of alcohol dehydrogenase or aldehyde dehydrogenase comprising a dehydrogenase cytochrome complex of *Gluconobacter* sp. or *Acetobacter* sp. (refer to the following references: Adachi, O., Tayama, K., Shinagawa, E., Matsushita, K. and Ameyama, M., Agr. Biol. Chem., 42, 2045-2056 (1978); Adachi, O., Miyagawa, E., Matsushita, K. and Ameyama, M., Agr. Biol. Chem., 42, 2331-2340 (1978); Ameyama, M. and Adachi, O., Methods Enzymol., 89, 450-457 (1982); Adachi, O., Tayama, K., Shinagawa, E., Matsushita, K. and Ameyama, M., Agr. Biol. Chem., 44, 503-515 (1980); Ameyama, M. and Adachi, O., Methods Enzymol., 89, 491-497 (1982)).

The results indicated a possibility that the oligomer complex of the GDH contained cytochrome. Therefore, it can be considered that the observed wavelength similar to that of cytochrome C is attributable to the β-subunit and was lost during the heat treatment, and thus the β-subunit consists of cytochrome C.

Example 9

A band containing the β-subunit obtained by the electrophoresis in Example 4 was excised, and the amino acid sequence was analyzed by using a peptide sequencer (PPSQ-10, Shimadzu Corporation). As a result, the N-terminus amino acid sequence consisting of 16 residues shown in SEQ ID NO: 5 could be obtained.

It was attempted to amplify a gene region encoding the aforementioned N-terminus amino acid sequence of 16 residues by PCR based on the peptide sequence. That is, two of PCR primers were designed, which had a nucleotide sequence on the forward side (SEQ ID NO: 6) corresponding to 5 residues at the N-terminus and a nucleotide sequence on the reverse side (SEQ ID NO: 7) corresponding to the antisense strand of 5 residues at the C-terminus in the peptide chain of the 16 residues. When PCR was performed in a conventional manner for the KS1 strain genome by using this pair of PCR primers, a gene fragment of about 50 by was amplified. When the nucleotide sequence of this gene fragment was determined in a conventional manner, a nucleotide sequence of 58 nucleotides containing the pair of PCR primers were decoded. Among these nucleotides, 18 nucleotides excluding the PCR primers were analyzed, and a gene sequence corresponding to a region from Pro, which was the 6th residue from the N-terminus side of the aforementioned 16 residues at the N-terminus of the β-subunit, to Arg, which was the 11th residue, was found (SEQ ID NO: 8). Thus, it was found that the amplified gene fragment included the gene fragment of the β-subunit.

Further, it was also found that the β-subunit existed after 22 amino acid residues following the α-subunit. This was based on a finding that, since the amino acid sequence at the N-terminus of the purified β-subunit determined in Example 4 matched 5 amino acid residues translated from the nucleotide sequence of the nucleotide numbers 2452 to 2466 in SEQ ID NO: 1, these sequences are identical.

Furthermore, it is inferred that the nucleotide sequence of the nucleotide numbers 2386 to 2451 in SEQ ID NO: 1 is the signal peptide of the β-subunit. The amino acid sequence encoded by this nucleotide sequence corresponds to the amino acid numbers 1 to 22 in the amino acid sequence of SEQ ID NO: 4.

Example 10

The purified enzyme and a commercially available NAD coenzyme GDH (abbreviated as "NAD-GDH") were added and mixed in 50 mM potassium phosphate buffer (pH 7.5) containing 0.1% Triton X-100 and 1 mM $CaCl_2$ at a concentration of 100 U/L each. Each solution was placed in a hot tank at 60° C., and the residual activity was measured.

TABLE 2

| | Residual relative activity (%) | |
|---|---|---|
| Time (min) | NAD-GDH | The enzyme GDH |
| 0 | 100 | 100 |
| 15 | 20 | 100 |
| 30 | 5 | 100 |

It was confirmed that the enzyme had surprising thermal stability in comparison with that of the currently commercially available GDH enzyme. It was found that the enzyme was a novel enzyme that is totally different from the commercially available NAD-GDH.

Example 10

Isolation of Gene Encoding α-Subunit of GDH

<1> Preparation of Chromosomal DNA from *Burkhorderia cepacia* KS1 Strain

A chromosomal gene was prepared from the *Burkhorderia cepacia* KS1 strain in a conventional manner. That is, the bacterial strain was shaken overnight at 34° C. by using a TL liquid medium (10 g of polypeptone, 1 g of yeast extract, 5 g of NaCl, 2 g of $KH_2PO_4$, 5 g of glucose in 1 L, pH 7.2). The grown cells were collected by using a centrifugal machine. The cells were suspended in a solution containing 10 mM NaCl, 20 mM Tris-HCl (pH 8.0), 1 mM EDTA, 0.5% SDS and 100 μg/ml proteinase K and treated at 50° C. for 6 hours. This mixture was added with an equivalent volume of phenol-chloroform and stirred at room temperature for 10 minutes, and then the supernatant was collected by using a centrifugal machine. The supernatant was added with sodium acetate at a final concentration of 0.3 M and overlaid with two-fold volume of ethanol to precipitate chromosomal DNA in the intermediate layer. The DNA was taken up with a glass rod, washed with 70% ethanol and dissolved in an appropriate amount of TE buffer to obtain a chromosomal DNA solution.

<2> Determination of N-Terminus Amino Acid Sequence of α-Subunit of GDH

GDH purified in the same manner as in Example 2 was concentrated by lyophilization and developed by SDS-electrophoresis using 12.5% polyacrylamide to isolate the α-subunit. The α-subunit thus obtained was transferred onto a polyvinylidene fluoride membrane, and then the N-terminus amino acid sequence was determined by using an amino acid sequencer (PPSQ-10, Shimadzu Corporation). As a result, it was found that the enzyme included a peptide sequence consisting of 11 residues of the amino acid numbers 2 to 12 in the amino acid sequence of SEQ ID NO: 3.

<3> Cloning of Gene Encoding α-Subunit

In an amount of 1 μg of the DNA prepared in <1> was subjected to limited digestion with a restriction enzyme Sau3AI and treated with calf intestinal alkaline phosphatase (CIAP). Separately, SuperCosI (obtained from STRATAGENE), which is a cosmid, was treated with BamHI, and the DNA fragment obtained by the limited digestion of the chromosomal DNA fragment derived from the α-15 strain with Sau3AI was incorporated into SuperCosI by using T4 DNA ligase. *Escherichia coli* XL-1 Blue MR (obtained from STRATAGENE) was transformed with the obtained recombinant DNA. Transformants were selected on an LB agar medium containing 10 μg/ml neomycin and 25 μg/ml ampicillin based on neomycin resistance and ampicillin resistance, which are antibiotic resistances of SuperCosI. The obtained transformants were cultured in the LB liquid medium. These transformant cells were collected and suspended in a reagent for measuring the GDH activity, and clones were selected by using dehydrogenase activity for glucose as an index. As a result, one clone strain showing the glucose dehydrogenase activity was obtained.

<4> Subcloning

DNA fragments containing the target gene were prepared from the cosmid, SuperCosI, containing the gene encoding the α-subunit obtained in <3>. The inserted gene fragments were excised from the cosmid by using a restriction enzyme NotI. These DNA fragments were treated with a restriction enzyme XbaI and incorporated into plasmid pUC18 digested with XbaI. The Escherichia coli DH5αMCR strain was transformed with the plasmid pUC18 containing each insert fragment, and colonies grown on an LB agar medium containing 50 μg/ml ampicillin were collected. The obtained transformants were cultured in a liquid LB medium and examined for the GDH activity in the cells in the same manner as in <3>. As a result, a strain showing the GDH activity was obtained from one transformant. The plasmid was extracted from this transformant, and the inserted DNA fragment was analyzed. As a result, an insert fragment of about 8.8 kbp was confirmed. This plasmid was designated as pKS1.

<5> Determination of Nucleotide Sequence

The nucleotide sequence of the inserted DNA fragment in pKS1 was determined according to the restriction enzyme analysis and a conventional method. As a result, the sequence of the DNA encoding the N-terminus amino acid sequence of the α-subunit found in <2> was confirmed in this inserted DNA fragment, and an open reading frame containing this sequence was found. The determined nucleotide sequence and the amino acid sequence that can be encoded by this nucleotide sequence are as shown in SEQ ID NOS: 1 and 3. The molecular weight of a protein obtained from the amino acid sequence was 59,831 Da and substantially matched the molecular weight of 60 kDa obtained by SDS-PAGE of the α-subunit of the *Burkhorderia cepacia* KS1 strain.

Since the nucleotide sequence of the α-subunit was determined, a vector was produced by using the aforementioned structural gene of the α-subunit, and a transformant was further produced with this vector.

First, a gene to be inserted into the vector was prepared as follows.

Amplification was performed by PCR using a genome fragment derived from the KS1 strain as a template so that a desired restriction enzyme site should be included. The following pair of oligonucleotide primers were used in PCR.

```
(Forward)
5'-CCCAAGCTTGGGCCGATACCGATACGCA-3'     (SEQ ID NO: 9)

(Reverse)
5'-GAGAAGCTTTCCGCACGGTCAGACTTCC-3'     (SEQ ID NO: 10)
```

The gene amplified by PCR was digested with a restriction enzyme HindIII and inserted into the expression vector pFLAG-CTS (SIGMA) at its cloning site, HindIII site. The obtained plasmid was designated as pFLAG-CTS/α.

The *Escherichia coli* DH5αMCR strain was transformed with the aforementioned plasmid pFLAG-CTS/α, and a colony grown on an LB agar medium containing 50 μg/ml ampicillin was collected.

Further, when the open reading frame of the pKS1 insert fragment was searched in the upstream of the α-subunit, a structural gene of 507 nucleotides encoding a polypeptide comprising 168 amino acid residues shown in SEQ ID NO: 2 (nucleotide numbers 258 to 761 in SEQ ID NO: 1) was newly found. This structural gene was considered to encode the γ-subunit.

Since it was found that the region encoding the γ-subunit existed upstream from the coding region of the α-subunit, a recombinant vector containing a gene having a polycistronic structure continuously including the γ-subunit and the α-subunit was produced, and a transformant introduced with this vector was constructed.

First, a gene to be inserted into the vector was prepared as follows.

Amplification was performed by PCR using a genome fragment of the KS1 strain continuously including the structural gene of the γ-subunit and the structural gene of the α-subunit as a template so that a desired restriction enzyme site should be included. The following pair of oligonucleotide primers were used for PCR.

```
(Forward)
5'-CATGCCATGGCACACAACGACAACACT-3'    (SEQ ID NO: 11)

(Reverse)
                                     (SEQ ID NO: 12)
5'-CCCAAGCTTGGGTCAGACTTCCTTCTTCAGC-3'
```

The 5' end and the 3' end of the gene amplified by PCR were digested with NcoI and HindIII, respectively, and the gene was inserted into the vector pTrc99A (Pharmacia) at its cloning site, NcoI/HindIII site. The obtained plasmid was designated as pTrc99A/γ+α.

The *Escherichia coli* DH5αMCR strain was transformed with the aforementioned plasmid pTrc99A/γ+α, and a colony grown on an LB agar medium containing 50 µg/ml ampicillin was collected.

Example 11

Production of α-Subunit of GDH by Recombinant *Escherichia Coli*

The α-subunit was produced by using the Escherichia coli DH5αMCR strain transformed with each of the aforementioned plasmids pKS1, pFLAG-CTS/α and pTrc99A/γ+α. Each transformant was inoculated into 3 ml of LB medium containing 50 µg/ml ampicillin and cultured at 37° C. for 12 hours, and cells were collected by using a centrifugal machine. The cells were disrupted by using a French press (1500 kgf), and a membrane fraction (10 mM potassium phosphate buffer, pH 6.0) was isolated by ultracentrifugation (160,400×g, 4° C., 90 minutes).

Example 12

Assay of Glucose

First, the GDH activity in each of the aforementioned membrane fractions was confirmed. Specifically, visual determination was performed by using a 10 mM potassium phosphate buffer (pH 7.0) containing 594 µM methylphenazine methosulfate (mPMS) and 5.94 µM 2,6-dichlorophenol-indopheol (DCIP). The results are shown below. The number of + represents the degree of color change from blue to colorless.

Membrane fraction of cultured transformant transformed with pFLAG-CTS/α: +
Membrane fraction of cultured transformant transformed with pKS1: ++
Membrane fraction of cultured transformant transformed with pTrc99A/γ+α: +++

The GDH activity of the membrane fraction of the cultured transformant transformed with pFLAG-CTS/α incorporated only with the α-subunit was the lowest, and the GDH activity of the membrane fraction of the cultured transformant transformed with pTrc99A/γ+α, with which a vector was efficiently constructed, was the highest.

Although the α-subunit was expressed even in the transformant transformed with a vector using only the structural gene of the α-subunit, the α-subunit could be efficiently obtained by using a vector containing the structural gene of the γ-subunit and the structural gene of the α-subunit in combination.

Glucose was assayed by using the glucose dehydrogenase of the present invention. The enzymatic activity of the glucose dehydrogenase (α-subunit) of the present invention was measured by using glucose at various concentrations. The GDH activity was measured in 10 mM potassium phosphate buffer (pH 7.0) containing 594 µM methylphenazine methosulfate (mPMS) and 5.94 µM 2,6-dichlorophenol-indopheol (DCIP). An enzyme sample and glucose as a substrate were added and incubated at 37° C., and change in the absorbance of DCIP at 600 nm was monitored by using a spectrophotometer. The absorbance decreasing rate was measured as an enzymatic reaction rate. Glucose could be quantified in the range of 0.01 to 1.0 mM by using the GDH of the present invention.

Example 13

Preparation and Evaluation of Glucose Sensor

The glucose dehydrogenase (25 units) of the present invention obtained in Example 2 was added with 20 mg of carbon paste and lyophilized. These were sufficiently mixed, applied only on a surface of a carbon paste electrode already filled with about 40 mg of carbon paste and polished on a filter paper. This electrode was treated in 10 mM MOPS buffer (pH 7.0) containing 1% glutaraldehyde at room temperature for 30 minutes and then treated in 10 mM MOPS buffer (pH 7.0) containing 20 mM lysine at room temperature for 20 minutes to block glutaraldehyde. This electrode was equilibrated in 10 mM MOPS buffer (pH 7.0) at room temperature for 1 hour or longer. The electrode was stored at 4° C.

By using the aforementioned electrode as a working electrode, an Ag/AgCl electrode as a reference electrode and a Pt electrode as a counter electrode, a response current value was measured upon addition of glucose. The 10 mM potassium phosphate buffer containing 1 mM methoxy-PMS was used as the reaction solution, and a potential of 100 mV was applied for the measurement.

Figure 6:
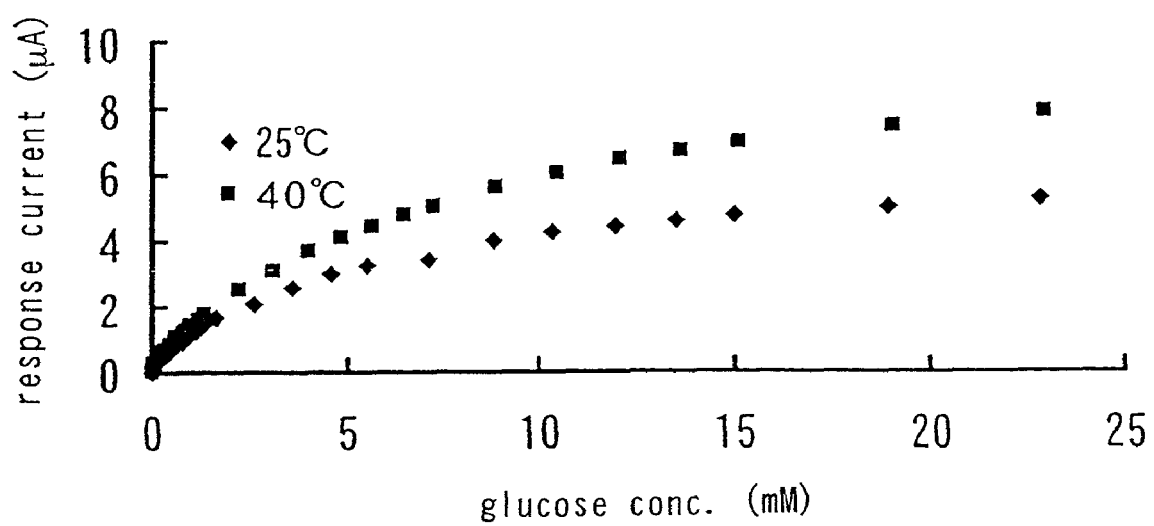
FIG. 6 shows responses of a glucose sensor using GDH obtained from a transformant to glucose at various temperatures.

Glucose concentration was measured by using the produced enzyme sensor. Glucose could be quantified in the range of 0.05 to 5.0 mM by using the enzyme sensor on which the glucose dehydrogenase of the present invention was immobilized (FIG. 6).

Example 14

Preparation and Evaluation of Glucose Sensor by GDH Obtained from Transformant

In an amount of 10 U of the α-subunit (249 U/mg protein) of the present invention obtained in Example 12 was added with 50 mg of carbon paste and lyophilized. These were sufficiently mixed, applied only on a surface of a carbon paste electrode already filled with about 40 mg of carbon paste and polished on a filter paper. This electrode was treated in a 10 mM MOPS buffer (pH 7.0) containing 1% glutaraldehyde at room temperature for 30 minutes and then treated in 10 mM MOPS buffer (pH 7.0) containing 20 mM lysine at room temperature for 20 minutes to block glutaraldehyde. This electrode was equilibrated in 10 mM MOPS buffer (pH 7.0) at room temperature for 1 hour or longer. The electrode was stored at 4° C.

By using the aforementioned electrode as a working electrode, an Ag/AgCl electrode as a reference electrode and a Pt electrode as a counter electrode, a response current value was measured upon addition of glucose. The 10 mM potassium phosphate buffer containing 1 mM methoxy-PMS was used as the reaction solution, and the measurement was performed for glucose aqueous solutions of various concentrations at 25° C. and 40° C. with applying a potential of 100 mV.

It was confirmed that, when the glucose concentration was measured by using the produced enzyme sensor, a current corresponding to each concentration was obtained.

INDUSTRIAL APPLICABILITY

According to the present invention, an enzyme that has high substrate specificity, can be produced at a low cost and is not affected by oxygen dissolved in a measurement sample, in particular, novel glucose dehydrogenase having superior thermal stability, and a method for producing the enzyme could be provided. Further, a novel bacterial strain of *Burkhorderia cepacia* producing the enzyme was obtained. A glucose sensor effective for measurement of glucose can also be provided by using an enzyme electrode containing the enzyme or the bacterial strain.

Further, since the glucose dehydrogenase gene, a peptide that enables efficient expression of the gene and a DNA encoding this peptide were found by the present invention, a large amount of GDH can be prepared by using recombinant DNA techniques based on the gene.

What is claimed is:

1. An isolated DNA encoding a protein having the amino acid sequence of SEQ ID NO: 2.

2. The isolated DNA according to claim 1, which comprises the nucleotide sequence of nucleotides 258 to 761 of SEQ ID NO: 1.

3. The isolated DNA according to claim 1, further comprising a DNA selected from the group consisting of
   (A) a DNA which encodes the protein which has the amino acid sequence of SEQ ID NO: 3;
   (B) a DNA which encodes the protein which has the amino acid sequence of SEQ ID NO: 3 including substitution, deletion, insertion or addition of 1 to 10 amino acid residues and a glucose dehydrogenase activity; and
   (C) a DNA which comprises the nucleotide sequence of nucleotides 764 to 2380 of SEQ ID NO: 1.

4. The isolated DNA according to claim 3, which comprises the nucleotide sequence of nucleotides 258 to 2380 of SEQ ID NO: 1.

5. The isolated DNA according to claim 3, which further comprises the nucleotide sequence of SEQ ID NO: 8, and a nucleotide sequence encoding a β-subunit of a glucose dehydrogenase.

6. A recombinant vector, capable of self-replication in a microbial cell, comprising the isolated DNA according to any one of claims 3 to 5.

7. A microbial host cell transformed with the recombinant vector according to claim 6.

8. A method for producing glucose dehydrogenase comprising the steps of culturing the transformant according to claim 7 to produce glucose dehydrogenase, and collecting the glucose dehydrogenase.

* * * * *

UNITED STATES PATENT AND TRADEMARK OFFICE
CERTIFICATE OF CORRECTION

| | | |
|---|---|---|
| PATENT NO. | : 7,960,156 B2 | Page 1 of 2 |
| APPLICATION NO. | : 12/764794 | |
| DATED | : June 14, 2011 | |
| INVENTOR(S) | : Koji Sode | |

It is certified that error appears in the above-identified patent and that said Letters Patent is hereby corrected as shown below:

Title Page 1, Line 12, item (56) Other Publications, "fro *Burkholderia*" should be changed to --for *Burkholderia*--

Title Page 1, Line 16, item (56) Other Publications, "Its Quatemary" should be changed to --Its Quaternary--

Column 2, Line 13, "lactone+NADPH+H." should be changed to --lactone+NADPH+$H^+$.--

Column 2, Line 61, "*Burkhorderia cepacia*" should be changed to --*Burkholderia cepacia*--

Column 2, Line 67, "genus *Burkhorderia*" should be changed to --genus *Burkholderia*--

Column 5, Line 45, "genus *Burkhorderia*" should be changed to --genus *Burkholderia*--

Column 5, Line 46, "*Burkhorderia* bacterium" should be changed to --*Burkholderia* bacterium--

Column 5, Line 47, "*Burkhorderia* bacterium" should be changed to --*Burkholderia* bacterium--

Column 5, Lines 48-49, "However, *Burkhorderia cepacia*," should be changed to --However, *Burkholderia cepacia*,--

Column 5, Line 49, "the *Burkhorderia cepacia* KS1" should be changed to --the *Burkholderia cepacia* KS1--

Column 5, Line 53, "as *Burkhorderia cepacia*" should be changed to --as *Burkholderia cepacia*--

Column 5, Line 55, "genus *Burkhorderia* can" should be changed to --genus *Burkholderia* can--

Column 5, Line 64, "*Burkhorderia cepacia* strains other than the *Burkhorderia*" should be changed to --*Burkholderia cepacia* strains other than the *Burkholderia*--

Column 8, Line 64, "2,6-dichlorophenol-indopheol" should be changed to --2,6-dichlorophenol-indophenol--

Column 11, Line 48, "collect GHD as an" should be changed to --collect GDH as an--

Column 11, Line 59, "obtain purified GHD." should be changed to --obtain purified GDH.--

Column 20, Line 15, "about 50 by was" should be changed to --about 50 bp was--

Signed and Sealed this
Twentieth Day of December, 2011

David J. Kappos
*Director of the United States Patent and Trademark Office*

CERTIFICATE OF CORRECTION (continued)
U.S. Pat. No. 7,960,156 B2

Column 23, Line 47, "indopheol (DCIP)." should be changed to --indophenol (DCIP).--

Column 24, Line 7, "5.94µM 2,6-dichlorophenol-indopheol (DCIP)." should be changed to --5.94µM 2,6-dichlorophenol-indophenol (DCIP).--

Column 35, Line 40, "<211> LENGTH : 28" should be changed to --<211> LENGTH : 29--

Columns 35-36, Line 46, "gagaagcttt ccgcacggtc agacttcc    28" should be changed to --gagaagcttt ccgcacggtc agacttcc    29--

SEQUENCE LISTING

```
<160> NUMBER OF SEQ ID NOS: 12

<210> SEQ ID NO 1
<211> LENGTH: 2467
<212> TYPE: DNA
<213> ORGANISM: Burkhorderia cepacia
<220> FEATURE:
<221> NAME/KEY: CDS
<222> LOCATION: (258)..(761)
<220> FEATURE:
<221> NAME/KEY: CDS
<222> LOCATION: (764)..(2380)
<220> FEATURE:
<221> NAME/KEY: CDS
<222> LOCATION: (2386)..(2466)

<400> SEQUENCE: 1
aagctttctg tttgattgca cgcgattcta accgagcgtc tgtgaggcgg aacgcgacat      60
gcttcgtgtc gcacacgtgt cgcgccgacg acacaaaaat gcagcgaaat ggctgatcgt    120
tacgaatggc tgacacattg aatggactat aaaaccattg tccgttccgg aatgtgcgcg    180
tacatttcag gtccgcgccg atttttgaga aatatcaagc gtggttttcc cgaatccggt    240
gttcgagaga aggaaac atg cac aac gac aac act ccc cac tcg cgt cgc       290
                    Met His Asn Asp Asn Thr Pro His Ser Arg Arg
                     1               5                  10 cac ggc gac gca gcc gca tca ggc atc acg cgg cgt caa tgg ttg caa      338
His Gly Asp Ala Ala Ala Ser Gly Ile Thr Arg Arg Gln Trp Leu Gln
             15                  20                  25 ggc gcg ctg gcg ctg acc gca gcg ggc ctc acg ggt tcg ctg aca ttg      386
Gly Ala Leu Ala Leu Thr Ala Ala Gly Leu Thr Gly Ser Leu Thr Leu
         30                  35                  40 cgg gcg ctt gca gac aac ccc ggc act gcg ccg ctc gat acg ttc atg      434
Arg Ala Leu Ala Asp Asn Pro Gly Thr Ala Pro Leu Asp Thr Phe Met
     45                  50                  55 acg ctt tcc gaa tcg ctg acc ggc aag aaa ggg ctc agc cgc gtg atc      482
Thr Leu Ser Glu Ser Leu Thr Gly Lys Lys Gly Leu Ser Arg Val Ile
 60                  65                  70                  75 ggc gag cgc ctg ctg cag gcg ctg cag aag ggc tcg ttc aag acg gcc      530
Gly Glu Arg Leu Leu Gln Ala Leu Gln Lys Gly Ser Phe Lys Thr Ala
                 80                  85                  90 gac agc ctg ccg cag ctc gcc ggc gcg ctc gcg tcc ggt tcg ctg acg      578
Asp Ser Leu Pro Gln Leu Ala Gly Ala Leu Ala Ser Gly Ser Leu Thr
             95                 100                 105 cct gaa cag gaa tcg ctc gca ctg acg atc ctc gag gcc tgg tat ctc      626
Pro Glu Gln Glu Ser Leu Ala Leu Thr Ile Leu Glu Ala Trp Tyr Leu
        110                 115                 120 ggc atc gtc gac aac gtc gtg att acg tac gag gaa gca tta atg ttc      674
Gly Ile Val Asp Asn Val Val Ile Thr Tyr Glu Glu Ala Leu Met Phe
    125                 130                 135
```

```
ggc gtc gtg tcc gat acg ctc gtg atc cgt tcg tat tgc ccc aac aaa      722
Gly Val Val Ser Asp Thr Leu Val Ile Arg Ser Tyr Cys Pro Asn Lys
140                 145                 150                 155 ccc ggc ttc tgg gcc gac aaa ccg atc gag agg caa gcc tg atg gcc       769
Pro Gly Phe Trp Ala Asp Lys Pro Ile Glu Arg Gln Ala     Met Ala
                160                 165                      1 gat acc gat acg caa aag gcc gac gtc gtc gtc gtt gga tcg ggt gtc      817
Asp Thr Asp Thr Gln Lys Ala Asp Val Val Val Val Gly Ser Gly Val
        5                   10                  15 gcg ggc gcg atc gtc gcg cat cag ctc gcg atg gcg ggc aag gcg gtg      865
Ala Gly Ala Ile Val Ala His Gln Leu Ala Met Ala Gly Lys Ala Val
        20                  25                  30 atc ctg ctc gaa gcg ggc ccg cgc atg ccg cgc tgg gaa atc gtc gag      913
Ile Leu Leu Glu Ala Gly Pro Arg Met Pro Arg Trp Glu Ile Val Glu
35                  40                  45                  50 cgc ttc cgc aat cag ccc gac aag atg gac ttc atg gcg ccg tac ccg      961
Arg Phe Arg Asn Gln Pro Asp Lys Met Asp Phe Met Ala Pro Tyr Pro
                55                  60                  65 tcg agc ccc tgg gcg ccg cat ccc gag tac ggc ccg ccg aac gac tac     1009
Ser Ser Pro Trp Ala Pro His Pro Glu Tyr Gly Pro Pro Asn Asp Tyr
            70                  75                  80 ctg atc ctg aag ggc gag cac aag ttc aac tcg cag tac atc cgc gcg     1057
Leu Ile Leu Lys Gly Glu His Lys Phe Asn Ser Gln Tyr Ile Arg Ala
            85                  90                  95 gtg ggc ggc acg acg tgg cac tgg gcc gcg tcg gcg tgg cgc ttc att     1105
Val Gly Gly Thr Thr Trp His Trp Ala Ala Ser Ala Trp Arg Phe Ile
100                 105                 110 ccg aac gac ttc aag atg aag agc gtg tac ggc gtc ggc cgc gac tgg     1153
Pro Asn Asp Phe Lys Met Lys Ser Val Tyr Gly Val Gly Arg Asp Trp
115                 120                 125                 130 ccg atc cag tac gac gat ctc gag ccg tac tat cag cgc gcg gag gaa     1201
Pro Ile Gln Tyr Asp Asp Leu Glu Pro Tyr Tyr Gln Arg Ala Glu Glu
                135                 140                 145 gag ctc ggc gtg tgg ggc ccg ggc ccc gag gaa gat ctg tac tcg ccg     1249
Glu Leu Gly Val Trp Gly Pro Gly Pro Glu Glu Asp Leu Tyr Ser Pro
            150                 155                 160 cgc aag cag ccg tat ccg atg ccg ccg ctg ccg ttg tcg ttc aac gag     1297
Arg Lys Gln Pro Tyr Pro Met Pro Pro Leu Pro Leu Ser Phe Asn Glu
            165                 170                 175 cag acc atc aag acg gcg ctg aac aac tac gat ccg aag ttc cat gtc     1345
Gln Thr Ile Lys Thr Ala Leu Asn Asn Tyr Asp Pro Lys Phe His Val
            180                 185                 190 gtg acc gag ccg gtc gcg cgc aac agc cgc ccg tac gac ggc cgc ccg     1393
Val Thr Glu Pro Val Ala Arg Asn Ser Arg Pro Tyr Asp Gly Arg Pro
195                 200                 205                 210 act tgt tgc ggc aac aac aac tgc atg ccg atc tgc ccg atc ggc gcg     1441
Thr Cys Cys Gly Asn Asn Asn Cys Met Pro Ile Cys Pro Ile Gly Ala
                215                 220                 225 atg tac aac ggc atc gtg cac gtc gag aag gcc gaa cgc gcc ggc gcg     1489
Met Tyr Asn Gly Ile Val His Val Glu Lys Ala Glu Arg Ala Gly Ala
            230                 235                 240 aag ctg atc gag aac gcg gtc gtc tac aag ctc gag acg ggc ccg gac     1537
Lys Leu Ile Glu Asn Ala Val Val Tyr Lys Leu Glu Thr Gly Pro Asp
            245                 250                 255 aag cgc atc gtc gcg gcg ctc tac aag gac aag acg ggc gcc gag cat     1585
Lys Arg Ile Val Ala Ala Leu Tyr Lys Asp Lys Thr Gly Ala Glu His
            260                 265                 270 cgc gtc gaa ggc aag tat ttc gtg ctc gcc gcg aac ggc atc gag acg     1633
Arg Val Glu Gly Lys Tyr Phe Val Leu Ala Ala Asn Gly Ile Glu Thr
275                 280                 285                 290
```

```
ccg aag atc ctg ctg atg tcc gcg aac cgc gat ttc ccg aac ggt gtc    1681
Pro Lys Ile Leu Leu Met Ser Ala Asn Arg Asp Phe Pro Asn Gly Val
            295                 300                 305 gcg aac agc tcg gac atg gtc ggc cgc aac ctg atg gac cat ccg ggc    1729
Ala Asn Ser Ser Asp Met Val Gly Arg Asn Leu Met Asp His Pro Gly
            310                 315                 320 acc ggc gtg tcg ttc tat gcg agc gag aag ctg tgg ccg ggc cgc ggc    1777
Thr Gly Val Ser Phe Tyr Ala Ser Glu Lys Leu Trp Pro Gly Arg Gly
            325                 330                 335 ccg cag gag atg acg tcg ctg atc ggt ttc cgc gac ggt ccg ttc cgc    1825
Pro Gln Glu Met Thr Ser Leu Ile Gly Phe Arg Asp Gly Pro Phe Arg
            340                 345                 350 gcg acc gaa gcg gcg aag aag atc cac ctg tcg aac ctg tcg cgc atc    1873
Ala Thr Glu Ala Ala Lys Lys Ile His Leu Ser Asn Leu Ser Arg Ile
355                 360                 365                 370 gac cag gag acg cag aag atc ttc aag gcc ggc aag ctg atg aag ccc    1921
Asp Gln Glu Thr Gln Lys Ile Phe Lys Ala Gly Lys Leu Met Lys Pro
            375                 380                 385 gac gag ctc gac gcg cag atc cgc gac cgt tcc gca cgc tac gtg cag    1969
Asp Glu Leu Asp Ala Gln Ile Arg Asp Arg Ser Ala Arg Tyr Val Gln
            390                 395                 400 ttc gac tgc ttc cac gaa atc ctg ccg caa ccc gag aac cgc atc gtg    2017
Phe Asp Cys Phe His Glu Ile Leu Pro Gln Pro Glu Asn Arg Ile Val
            405                 410                 415 ccg agc aag acg gcg acc gat gcg atc ggc att ccg cgc ccc gag atc    2065
Pro Ser Lys Thr Ala Thr Asp Ala Ile Gly Ile Pro Arg Pro Glu Ile
            420                 425                 430 acg tat gcg atc gac gac tac gtg aag cgc ggc gcc gcg cat acg cgc    2113
Thr Tyr Ala Ile Asp Asp Tyr Val Lys Arg Gly Ala Ala His Thr Arg
435                 440                 445                 450 gag gtc tac gcg acc gcc gcg aag gtg ctc ggc ggc acg gac gtc gtg    2161
Glu Val Tyr Ala Thr Ala Ala Lys Val Leu Gly Gly Thr Asp Val Val
            455                 460                 465 ttc aac gac gaa ttc gcg ccg aac aat cac atc acg ggc tcg acg atc    2209
Phe Asn Asp Glu Phe Ala Pro Asn Asn His Ile Thr Gly Ser Thr Ile
            470                 475                 480 atg ggc gcc gat gcg cgc gac tcc gtc gtc gac aag gac tgc cgc acg    2257
Met Gly Ala Asp Ala Arg Asp Ser Val Val Asp Lys Asp Cys Arg Thr
            485                 490                 495 ttc gac cat ccg aac ctg ttc att tcg agc agc gcg acg atg ccg acc    2305
Phe Asp His Pro Asn Leu Phe Ile Ser Ser Ser Ala Thr Met Pro Thr
            500                 505                 510 gtc ggt acc gta aac gtg acg ctg acg atc gcc gcg ctc gcg ctg cgg    2353
Val Gly Thr Val Asn Val Thr Leu Thr Ile Ala Ala Leu Ala Leu Arg
515                 520                 525                 530 atg tcg gac acg ctg aag aag gaa gtc tgacc gtg cgg aaa tct act ctc    2403
Met Ser Asp Thr Leu Lys Lys Glu Val       Val Arg Lys Ser Thr Leu
            535                            1               5 act ttc ctc atc gcc ggt tgc ctc gcg ttg ccg ggc ttc gcg cgc gcg    2451
Thr Phe Leu Ile Ala Gly Cys Leu Ala Leu Pro Gly Phe Ala Arg Ala
            10                  15                  20 gcc gat gcg gcc gat c                                                2467
Ala Asp Ala Ala Asp
            25

<210> SEQ ID NO 2
<211> LENGTH: 168
<212> TYPE: PRT
<213> ORGANISM: Burkhorderia cepacia

<400> SEQUENCE: 2
```

```
Met His Asn Asp Asn Thr Pro His Ser Arg Arg His Gly Asp Ala Ala
  1               5                  10                  15

Ala Ser Gly Ile Thr Arg Arg Gln Trp Leu Gln Gly Ala Leu Ala Leu
             20                  25                  30

Thr Ala Ala Gly Leu Thr Gly Ser Leu Thr Leu Arg Ala Leu Ala Asp
         35                  40                  45

Asn Pro Gly Thr Ala Pro Leu Asp Thr Phe Met Thr Leu Ser Glu Ser
     50                  55                  60

Leu Thr Gly Lys Lys Gly Leu Ser Arg Val Ile Gly Glu Arg Leu Leu
 65                  70                  75                  80

Gln Ala Leu Gln Lys Gly Ser Phe Lys Thr Ala Asp Ser Leu Pro Gln
                 85                  90                  95

Leu Ala Gly Ala Leu Ala Ser Gly Ser Leu Thr Pro Glu Gln Glu Ser
            100                 105                 110

Leu Ala Leu Thr Ile Leu Glu Ala Trp Tyr Leu Gly Ile Val Asp Asn
            115                 120                 125

Val Val Ile Thr Tyr Glu Glu Ala Leu Met Phe Gly Val Val Ser Asp
        130                 135                 140

Thr Leu Val Ile Arg Ser Tyr Cys Pro Asn Lys Pro Gly Phe Trp Ala
145                 150                 155                 160

Asp Lys Pro Ile Glu Arg Gln Ala
                165
```

<210> SEQ ID NO 3
<211> LENGTH: 539
<212> TYPE: PRT
<213> ORGANISM: Burkhorderia cepacia

<400> SEQUENCE: 3

```
Met Ala Asp Thr Asp Thr Gln Lys Ala Asp Val Val Val Val Gly Ser
  1               5                  10                  15

Gly Val Ala Gly Ala Ile Val Ala His Gln Leu Ala Met Ala Gly Lys
             20                  25                  30

Ala Val Ile Leu Leu Glu Ala Gly Pro Arg Met Pro Arg Trp Glu Ile
         35                  40                  45

Val Glu Arg Phe Arg Asn Gln Pro Asp Lys Met Asp Phe Met Ala Pro
     50                  55                  60

Tyr Pro Ser Ser Pro Trp Ala Pro His Pro Glu Tyr Gly Pro Pro Asn
 65                  70                  75                  80

Asp Tyr Leu Ile Leu Lys Gly Glu His Lys Phe Asn Ser Gln Tyr Ile
                 85                  90                  95

Arg Ala Val Gly Gly Thr Thr Trp His Trp Ala Ala Ser Ala Trp Arg
            100                 105                 110

Phe Ile Pro Asn Asp Phe Lys Met Lys Ser Val Tyr Gly Val Gly Arg
            115                 120                 125

Asp Trp Pro Ile Gln Tyr Asp Asp Leu Glu Pro Tyr Tyr Gln Arg Ala
        130                 135                 140

Glu Glu Glu Leu Gly Val Trp Gly Pro Gly Pro Glu Glu Asp Leu Tyr
145                 150                 155                 160

Ser Pro Arg Lys Gln Pro Tyr Pro Met Pro Pro Leu Pro Leu Ser Phe
                165                 170                 175

Asn Glu Gln Thr Ile Lys Thr Ala Leu Asn Asn Tyr Asp Pro Lys Phe
            180                 185                 190

His Val Val Thr Glu Pro Val Ala Arg Asn Ser Arg Pro Tyr Asp Gly
            195                 200                 205
```

```
Arg Pro Thr Cys Cys Gly Asn Asn Cys Met Pro Ile Cys Pro Ile
    210                 215                 220

Gly Ala Met Tyr Asn Gly Ile Val His Val Glu Lys Ala Glu Arg Ala
225                 230                 235                 240

Gly Ala Lys Leu Ile Glu Asn Ala Val Val Tyr Lys Leu Glu Thr Gly
                245                 250                 255

Pro Asp Lys Arg Ile Val Ala Ala Leu Tyr Lys Asp Lys Thr Gly Ala
            260                 265                 270

Glu His Arg Val Glu Gly Lys Tyr Phe Val Leu Ala Ala Asn Gly Ile
        275                 280                 285

Glu Thr Pro Lys Ile Leu Leu Met Ser Ala Asn Arg Asp Phe Pro Asn
    290                 295                 300

Gly Val Ala Asn Ser Ser Asp Met Val Gly Arg Asn Leu Met Asp His
305                 310                 315                 320

Pro Gly Thr Gly Val Ser Phe Tyr Ala Ser Glu Lys Leu Trp Pro Gly
                325                 330                 335

Arg Gly Pro Gln Glu Met Thr Ser Leu Ile Gly Phe Arg Asp Gly Pro
            340                 345                 350

Phe Arg Ala Thr Glu Ala Ala Lys Lys Ile His Leu Ser Asn Leu Ser
        355                 360                 365

Arg Ile Asp Gln Glu Thr Gln Lys Ile Phe Lys Ala Gly Lys Leu Met
    370                 375                 380

Lys Pro Asp Glu Leu Asp Ala Gln Ile Arg Asp Arg Ser Ala Arg Tyr
385                 390                 395                 400

Val Gln Phe Asp Cys Phe His Glu Ile Leu Pro Gln Pro Glu Asn Arg
                405                 410                 415

Ile Val Pro Ser Lys Thr Ala Thr Asp Ala Ile Gly Ile Pro Arg Pro
            420                 425                 430

Glu Ile Thr Tyr Ala Ile Asp Asp Tyr Val Lys Arg Gly Ala Ala His
        435                 440                 445

Thr Arg Glu Val Tyr Ala Thr Ala Ala Lys Val Leu Gly Gly Thr Asp
    450                 455                 460

Val Val Phe Asn Asp Glu Phe Ala Pro Asn Asn His Ile Thr Gly Ser
465                 470                 475                 480

Thr Ile Met Gly Ala Asp Ala Arg Asp Ser Val Val Asp Lys Asp Cys
                485                 490                 495

Arg Thr Phe Asp His Pro Asn Leu Phe Ile Ser Ser Ser Ala Thr Met
            500                 505                 510

Pro Thr Val Gly Thr Val Asn Val Thr Leu Thr Ile Ala Ala Leu Ala
        515                 520                 525

Leu Arg Met Ser Asp Thr Leu Lys Lys Glu Val
    530                 535

<210> SEQ ID NO 4
<211> LENGTH: 27
<212> TYPE: PRT
<213> ORGANISM: Burkhorderia cepacia

<400> SEQUENCE: 4

Val Arg Lys Ser Thr Leu Thr Phe Leu Ile Ala Gly Cys Leu Ala Leu
1               5                   10                  15

Pro Gly Phe Ala Arg Ala Ala Asp Ala Ala Asp
            20                  25

<210> SEQ ID NO 5
```

```
<211> LENGTH: 16
<212> TYPE: PRT
<213> ORGANISM: Burkhorderia cepacia

<400> SEQUENCE: 5

Ala Asp Ala Ala Asp Pro Ala Leu Val Lys Arg Gly Glu Tyr Leu Ala
 1               5                  10                  15

<210> SEQ ID NO 6
<211> LENGTH: 15
<212> TYPE: DNA
<213> ORGANISM: Artificial Sequence
<220> FEATURE:
<223> OTHER INFORMATION: Description of Artificial Sequence: primer

<400> SEQUENCE: 6
gcggatgcgg cggat                                                        15

<210> SEQ ID NO 7
<211> LENGTH: 15
<212> TYPE: DNA
<213> ORGANISM: Artificial Sequence
<220> FEATURE:
<223> OTHER INFORMATION: Description of Artificial Sequence: primer

<400> SEQUENCE: 7
cgccagatat tcgcc                                                        15

<210> SEQ ID NO 8
<211> LENGTH: 18
<212> TYPE: DNA
<213> ORGANISM: Artificial Sequence
<220> FEATURE:
<223> OTHER INFORMATION: Description of Artificial Sequence: primer

<400> SEQUENCE: 8
ccggcgctgg tgaaacgc                                                     18

<210> SEQ ID NO 9
<211> LENGTH: 28
<212> TYPE: DNA
<213> ORGANISM: Artificial Sequence
<220> FEATURE:
<223> OTHER INFORMATION: Description of Artificial Sequence: primer

<400> SEQUENCE: 9
cccaagcttg ggccgatacc gatacgca                                          28

<210> SEQ ID NO 10
<211> LENGTH: 28
<212> TYPE: DNA
<213> ORGANISM: Artificial Sequence
<220> FEATURE:
<223> OTHER INFORMATION: Description of Artificial Sequence: primer

<400> SEQUENCE: 10
gagaagcttt ccgcacggtc agacttcc                                          28

<210> SEQ ID NO 11
<211> LENGTH: 27
<212> TYPE: DNA
<213> ORGANISM: Artificial Sequence
<220> FEATURE:
<223> OTHER INFORMATION: Description of Artificial Sequence: primer

<400> SEQUENCE: 11
catgccatgg cacacaacga caacact                                           27
```

```
<210> SEQ ID NO 12
<211> LENGTH: 31
<212> TYPE: DNA
<213> ORGANISM: Artificial Sequence
<220> FEATURE:
<223> OTHER INFORMATION: Description of Artificial Sequence: primer

<400> SEQUENCE: 12
cccaagcttg ggtcagactt ccttcttcag c                           31
```